United States Patent
Zhang et al.

(10) Patent No.: US 11,254,952 B2
(45) Date of Patent: Feb. 22, 2022

(54) TRANSCRIPTIONAL REGULATORY ELEMENT AND ITS USE IN ENHANCING THE EXPRESSION OF HETEROLOGOUS PROTEIN

(71) Applicant: WuXi Biologies Ireland Limited, Dublin (IE)

(72) Inventors: Zheng Zhang, Shanghai (CN); Xiaolu Li, Shanghai (CN); Yuchen Zhang, Shanghai (CN); Yarong Li, Shanghai (CN); Huifang Dong, Shanghai (CN); Jill Cai, Shanghai (CN); Weichang Zhou, Shanghai (CN); Chris Chen, Shanghai (CN); Lili Mu, Shanghai (CN); Chuanlong Tang, Shanghai (CN)

(73) Assignee: WuXi Biologies Ireland Limited, Dundalk (IE)

( * ) Notice: Subject to any disclaimer, the term of this patent is extended or adjusted under 35 U.S.C. 154(b) by 0 days.

(21) Appl. No.: 17/268,360

(22) PCT Filed: Aug. 14, 2019

(86) PCT No.: PCT/CN2019/100549
§ 371 (c)(1),
(2) Date: Feb. 12, 2021

(87) PCT Pub. No.: WO2020/034986
PCT Pub. Date: Feb. 20, 2020

(65) Prior Publication Data
US 2021/0254100 A1 Aug. 19, 2021

(30) Foreign Application Priority Data
Aug. 14, 2018 (WO) ................ PCT/CN2018/100467

(51) Int. Cl.
| C12N 15/85 | (2006.01) |
| C07K 16/24 | (2006.01) |
| C07K 16/28 | (2006.01) |
| C12N 15/67 | (2006.01) |

(52) U.S. Cl.
CPC ............ *C12N 15/85* (2013.01); *C07K 16/241* (2013.01); *C07K 16/2818* (2013.01); *C12N 15/67* (2013.01); *C12N 2830/30* (2013.01); *C12N 2830/85* (2013.01)

(58) Field of Classification Search
CPC .... C12N 15/85; C12N 15/67; C12N 2830/30; C12N 2830/85
See application file for complete search history.

(56) References Cited

U.S. PATENT DOCUMENTS

| 9,902,969 | B2 | 2/2018 | Lee et al. |
| 2011/0076760 | A1 | 3/2011 | Silla et al. |
| 2016/0159926 | A1 | 6/2016 | Hwang et al. |

FOREIGN PATENT DOCUMENTS

| CN | 102459586 | 5/2012 |
| CN | 103834686 | 6/2014 |
| CN | 105255895 | 1/2016 |
| CN | 106432501 | 2/2017 |
| CN | 106987559 | 7/2017 |
| JP | 2007525956 | 9/2007 |
| WO | WO 20050008888 A2 | 1/2005 |
| WO | WO 2017184831 | 10/2017 |
| WO | WO 2018050111 | 3/2018 |

OTHER PUBLICATIONS

Boshart et al., "A very strong enhancer is located upstream of an immediate early gene of human cytomegalovirus," Cell, Jun. 1985, 41(2):521-530.

Cole et al., "Identification of sequences in the herpes simplex virus thymidine kinase gene required for efficient processing and polyadenylation," Mol. Cell Biol., Aug. 1985, 5(8):2104-2113.

Fitzgerald et al., "The sequence 5'-AAUAAA-3'forms parts of the recognition site for polyadenylation of late SV40 mRNAs," Cell, Apr. 1981, 24(1):251-260.

Gatignol et al., "Bleomycin resistance conferred by a drug-binding protein," FEBS Lett., Mar. 28, 1988, 230(1-2):171-175.

Gurtu et al., "IRES bicistronic expression vectors for efficient creation of stable mammalian cell lines," Biochem. Biophys. Res. Commun., Dec. 4, 1996, 229(1):295-298.

Kim et al., "Use of the human elongation factor 1 alpha promoter as a versatile and efficient expression system," Gene, Jul. 16, 1990, 91(2):217-223.

Kimur et al., "Blasticidin S deaminase gene from *Aspergillus terreus* (BSD): a new drug resistance gene for transfection of mammalian cells," Biochim. Biophys. Acta., Nov. 22, 1994, 1219(3):653-659.

Southern et al., "Transformation of mammalian cells to antibiotic resistance with a bacterial gene under control of the SV40 early region promoter," J Mol. Appl. Genet., 1982, 1(4):327-341, 1 page (Abstract Only).

Yanisch-Perron et al., "Improved M13 phage cloning vectors and host strains: nucleotide sequences of the M13mpl8 and pUC19 vectors," Gene, 1985, 33(1):103-119.

(Continued)

*Primary Examiner* — Antonio Galisteo Gonzalez
(74) *Attorney, Agent, or Firm* — Fish & Richardson P.C.

(57) ABSTRACT

Provided is a polynucleotide, the polynucleotide can be used as a WXRE transcriptional regulatory element used to increase the protein expression level of a protein expression system. A protein expression vector or a protein expression system comprising the above-mentioned WXRE transcriptional regulatory element as well as the use thereof are also provided. The use of the WXRE transcriptional regulatory element can increase the expression level of a heterologous protein greatly with its biological activity unchanged.

20 Claims, 6 Drawing Sheets
Specification includes a Sequence Listing.

(56) References Cited

OTHER PUBLICATIONS

Jahandar et al. "Effect of Cysteamine on Cell Growth and IgG4 Production in Recombinant Sp2.0 Cells" Iranian Journal of Pharmaceutical Research, 2015, 14(1): 177-187.
NCBI Reference Sequence: NW_003613694.1 Cricetulus griseus unplaced genomic scaffold, CriGri_1.0 scaffold689, whole genome shotgun sequence, May 27, 2016 (May, 27, 2016).
NCBI Reference Sequence: NW_003614323.1 Cricetulus griseus unplaced genomic scaffold, CriGri_1.0 scaffold928, whole genome shotgun sequence, May 27, 2016 (May 27, 2016).
NCBI Reference Sequence: NW_003646628.1 Cricetulus griseus unplaced genomicscaffold, CriGri_1.0 scaffold24313, whole genome shotgun sequence, May 27, 2016 (May 27, 2016).
NCBI Reference Sequence: NW_003619752.1 Cricetulus griseus unplaced genomic scaffold, CriGri_1.0 scaffold27679, whole genome shotgun sequence, May 27, 2016 (May 27, 2016).
NCBI Reference Sequence: NW_003630025.1 Cricetulus griseus unplaced genomic scaffold, CriGri_1.0 scaffold C41403100, whole genome shotgun sequence, May 27, 2016 (May 27, 2016).
NCBI Reference Sequence: NW_003614865.1 Cricetulus griseus unplaced genomic scaffold, CriGri_1.0 scaffold3125, whole genome shotgun sequence, May 27, 2016 (May 27, 2016).
NCBI Reference Sequence: NW_003615153.1 Cricetulus griseus unplaced genomic scaffold, CriGri_1.0 scaffold537, whole genome shotgun sequence, May 27, 2016 (May 27, 2016).
PCT International Search Report in International Appln. No. PCT/CN2019/100549, dated Nov. 12, 2019, 7 pages.
Li et al., "Research Advance in Genome-wide Identification of Transcription Regulatory Elements," Biotechnology Bulletin, Oct. 31, 2014, 10:64-70, 7 pages (with English Abstract).
PCT International Preliminary Report on Patentability in International Appln. No. PCT/CN2018/100467, dated Feb. 16, 2021, 5 pages.
PCT International Search Report and Written Opinion in International Appln. No. PCT/CN2018/100467, dated May 27, 2019, 11 pages.
Yang et al., "Sterol-resistant transcription in CHO cells caused by gene rearrangement that truncates SREBP-2," Genes and Development, Aug. 15, 1994, 8(15):1910-1919.
Cricetulus griseus unplaced genomic scaffold, CriGri_1.0 scaffold537,whole genomic scaffold, CriGri_1.0 scaffold537, whole genome shotgun sequence, May 27, 2016, 98 pages.
Cricetulus griseus unplaced genomic scaffold, CriGri_1.0 scaffold928,whole genome shotgun sequence, May 27, 2016, 246 pages.
Wang et al., A simplified universal genomic DNA extraction protocol suitable for PCR, Genet. Mol. Res., Mar. 29, 2011, 10(1):519-525.
EP Office Action in European Appln. No. 19850474.8, dated Oct. 29, 2021, 6 pages.
Ng et al., "Regulation of the human β-actin promoter by upstream and intron domains," Nucleic Acids Research, Jan. 25, 1989, 17(2):601-615.

SEQUENCE LISTING

```
<160> NUMBER OF SEQ ID NOS: 23

<210> SEQ ID NO 1
<211> LENGTH: 27
<212> TYPE: DNA
<213> ORGANISM: Artificial Sequence
<220> FEATURE:
<223> OTHER INFORMATION: PCR primer

<400> SEQUENCE: 1 gcaaaaagg gaataagggc gacacgg                                          27

<210> SEQ ID NO 2
<211> LENGTH: 28
<212> TYPE: DNA
<213> ORGANISM: Artificial Sequence
<220> FEATURE:
<223> OTHER INFORMATION: PCR primer

<400> SEQUENCE: 2
catagcccat atatggagtt ccgcgtta                                        28

<210> SEQ ID NO 3
<211> LENGTH: 3619
<212> TYPE: DNA
<213> ORGANISM: Chinese hamster

<400> SEQUENCE: 3
gatctgcctg cctctgcccc gtgagtgctg ggattaaagg ccagcaccgc catgcctggc     60
ctcctttaag tgcaggtgta gcacgccaga aatacccctgc tggtgacagt gtgagccaca    120
```

```
tgcgtgagac tgctgcagag gtcccagctt aggttgtgcc cttctttctt gagaaatgtc    180
ttacttggtg attttgagtg gaaacatgta tttagctgac atatgagcct agtctttat     240 gtataaatgt gtgttatatt tctagataca aaatattaa aaattagaaa tcttcagggc     300
tggagagggg ttcattggtt aagagctcat tggttaaggg ctgctcctgt ataggacccg    360
ggttacctgt cagcaccgta tgacggctct caaccatctg cagctcccgt tccagaggac    420
ccagtgtctt cttctggcct ctacagacat acatatagac aaaacaccca tacacaaaaa    480
tttaattaga aatcttaatt tttttctttc aattttctag attgactggg gataacttt     540 ttgttaactt tactgtcttg aggataacgt tcagtatgag ttgtatttct agagtttgtc    600 tttatttta ggcaaaaata acctttatta ccattttggg gggtgactgt tttacaactt     660
ttccaacttc ctgcttcatc tcttgtgtcc tatataggcc cctatttact gtcattatta    720
gagataggac ttgatgtcat gtcaactcca tctttgttat aaatctcaag aagagctaat    780
ttcttttgtg ttattacaac caaaaataaa caaggtagct tataaacagt gacttatttt    840
tatagttcta gatatgggaa gatcatggtg acagtagatt caatgtctag ttggaagttg    900
actcttcttc atagatggaa tccttgctat aatataatct caggatggaa gggatgagct    960
aagccctctg ggatctctta ttaatctgtt cattcattta cttattgcat agtgctctaa   1020
ttctgttcat ggagactctg ttcttacaca ttaggtggtt agggagggac atgatcaatc   1080
aggacatagg agcaacaata atttttatta tatttcccaa aatacatggc agttcctgac   1140
cttgctttat tactgcaaac atacagcttg tggccattgg acttagccat atgagaaatg   1200
taagaattta ttttatattg tagctgcaaa tggtaggttc atcaaattgt gccttaagtt   1260
cacatcttaa tttgctacaa aaaaaaaaga ggagtagtgt aagttacatt taattttcaa   1320
ttacttagta acagtttgta agtgctactt gatcctgttt tatatctagc attgagtata   1380
gatcaacaag tgtttcaatt cttgtttgga catgctgttc tctccttcat cacaagttac   1440
ttctggctaa acaaggcaca aatttcgcat gaccaccaat ccaaggacag ggcgacaatt   1500
ttaatgagtt tcattgagag ctggccaact gagcatctgt tccttttgtt ttcctgtacg   1560
tggtaagcca gtgtttctac actccttagc cttgttgctg tgtgtatagt gtggggtgga   1620 tttgttttg ctgttctttt ttcttttttc taccctctac ttcagtggtg cacggttaga    1680
aatcttgtgg cgtctggcac ggtggtataa ttccttccat gctcttgggt gaggaaataa   1740
gtttgctcat tgctgctcat cagtctgttt cacttgctcc cagatggtga ccttctcgtc   1800 ccattccttgc ttgtttaac attattctga cacctatttt ctttcattgt ccccttaacc   1860
actctaattg aataatgatt tctgtaattt ccatttggaa cacaaccagc ttcctggttc   1920
cttttattgg cccacatcct gtcttctagt tcattgcttc agatttgagc caaatcatca   1980
aataaaaata cgtaactgaa aaaatgtttt attgcagtgg cctcctctag catggcaaca   2040
atgagagttt tccttttctta ttgctaaaca tgttatatct gtctcatgat tcatactgt    2100 ctctcctggc ctcatttact gcttgacctt taaaagaaat gactcaaaga tattttgta    2160 gttctgtaag catttctcta gttccttgttc ttcacccttta gttcttaaca gtagttttgt  2220
ctgctacact gacgtggctg tgaggacttt ccttcagaaa ctggcgtctg atactgattc   2280
aaactggtct ccattgtggc ctacatgtcc agctgtctcc atgtaacgcc actgaaatac   2340
agtgaagcca gccttttttt ccccccttatg gttcaaagca actgaatttc agtcagagta  2400
attttggttt gggtatcaat actaattgta gtcttagacc ttttaattat tacttgtttg   2460
```

```
cattttacag aagacattgg tccttctcaa aagcagagat gaaacctgta gtattttgtg    2520
tgtagttttc ctctgctggt tgccctgtaa ctattcagtt cctgtaagga agcacagctg    2580
cttcataagc taccttaggc tgacagcagt ctcctgaaag aaagagttca agaaagaaac    2640
atttaaaaat aaaaatgggg aggggtccaa gtagtatttg aagccatgaa atatcttgaa    2700
tatagtttgc ttttttgttt tgttttgtct gtctgtctgt ccgatgtagc tttggccata    2760
tcaaccaggc tgtccttgaa ctcacagaaa tccacctgcc tccgcctccc aagtgctgga    2820
tgcaccacca tgccagctag tttgcttttt agagcatctc atctgctgct cacagccctg    2880 gtgcttatg ggatttgttt ggggaacatg atgagctcta tatttattgt agctttaaat    2940
ggacagcggt tattgactgt cagcttagtc tttaaaatct ataatcacat tgtacctaat    3000
tgtcaacctt catgttttt aattatgaaa aaaactgaga acattaattt ttatgttatc    3060
ttgttattga ctttattgaa atactacaga aaattttggt ttgaggcttt tccataattt    3120
acccttacac ctcacacccc ttccataaac atgtgcagtt aaaattgaat tgttcgggca    3180
cttctacctt gatacctggc ctacagtggg aaaggtctgt ctttctttgg aataagccca    3240
tcagtggcct tgtgtacatt ctgtattttt gttgtttgtt attactgttt tttacttggg    3300
actaataatc tgtttgaaac tgactgagat agaaagatgt gatgttcctt cccactcact    3360
ccggattttg atagaagact tgttttattt atttccaaaa ttatatccgc aggaaacaag    3420
ctgtttaaat tcagattatg ctgaagcaaa atggtcctgg tatgagaagc aacgtgctgt    3480
tttacgagca cagagtccct tttctcataa ctgattgata gtaaatattt tcctgaagaa    3540
ttattgccaa ccatgaacag tgcaactgtt tcacttttt tccgtgctac ttgctgtacc    3600
agccattgtc ggtaattaa                                                 3619

<210> SEQ ID NO 4
<211> LENGTH: 1114
<212> TYPE: DNA
<213> ORGANISM: Chinese hamster

<400> SEQUENCE: 4
gatctgaagt ttggatctgc agaacccaca caaaggccta cgggcttagt agtgtacctg      60
caatttcagc acttggaagg ctgagaaagg atcccaaggg cagctggcta gctaggctag     120
tgttagctga gagctctggg ttcgtggagc gactctggtt cagtgaataa gatagagagt     180
gacatcagct ttgggcttcc acagcaaatg agctcacttg catgcaaaca gaaatgcaaa     240
cacatgcaca aagcaaaaca aaaggaacac aggccaaagg tgggtcattc ctataccatc     300
ccctcagcag ggtgcagtcc ccacaccctg acccagttcc ctcatgatgt tagagaaaat     360
aactttgccc ccttcaacga acatttcagc tccagaaac ctggcccact ttgaaagctt     420
taattagaaa tgtgcaatta cccggaacag atgtctgttg tgattgtgga gacataggtt     480
aaagaatcac acagcagttt gcgtggttac agaaaggttg caagtaactt taaaacacag     540
tttttggtaa gtctccaaca tgttacctaa catgcatgg cctcgattac atgtaagcag     600
tgagtctccg gctgcctggt ttgtgagggt aatgtacttc agcaatagtg ctgaggctgt     660
acagtgagtg actcatcacc ctaaaaaagt atcgaattcc agtcttcaga gttagctttc     720
agtaaaacca agtcagtggt gaaatggctc agtaggtaag ggcacccgct gccaagccca     780
agacctgtgt cctgtccctg ggatccagtt ggtggaaaga gagaacggac tcctgcaagg     840
tggcctctga cctacatgcc tgaattctgc cagacattaa gtaaaacaa acgcaaaaag     900 ggaagtgggc tcacgcataa ggcactcact ggactctact cttctactct gtggttactt     960
```

```
tttggtgttc aagcatacca taccttgatc tacatgattt ttactccaaa gacacagcca    1020
gggtaatgtt gtgtgatgga tcagtcttat ttgttacttg tttactagta cttactgaga    1080
ttgtcgatgg ctttaatgtc aacatgagtg tgga                                1114
```

<210> SEQ ID NO 5
<211> LENGTH: 4068
<212> TYPE: DNA
<213> ORGANISM: Chinese hamster

<400> SEQUENCE: 5

```
gatcttctag gtctggctct gagttgaaag gctctgatgc tgggcgaaac atctctcctc      60
tggggctcag ttttctcatc tgttagaaaa ggacacagct gacctgttgg cttctaatag     120
ttggacagag gctaggattc tgagtctcat tttactacaa atattctttt aatttcttaa     180
gtcactaaac agcatcagca aggcagggtc gagacatgcg agcaagaatg agattggatt     240
ctgactcagg tttcaacttg ctgtcaatta ctgacaatgt aagttcattc atcttataga     300
cttttgtaga acttttgttt ctctccacta taatttcgtt actgttccat attacagtat     360
gctaaagtta atggtaaaag ttctcacaga attcctagtc ttttcctctt catatttaat     420
ctcctttcct tcctcctgtc cttactcatt gtgaaattct cttttgtatg catgacttgg     480
aaacatattt ccttggtggt aaggtagtag gagacaattt attcacttttt cacgtatgtc     540 gtaattggca tattgctgat aaagttttttc aaccatggga acatggtctt gtaagaatta     600
tttcacattt tcccagtcc aagcccataa tgaaaattga ttctgaattt tttctgtatt     660
tttaattctt ctgtttgcag ttgtaggaga ataaccctgc agcatctgag agaccaagct     720
aattacaaga atgactagaa atcctttgca ttttttaaaac aatttttatac atatgtcact     780 ttgtctttct aaaaaataaa aataaaaaaa atacctaaga gccgagtttg tgttaaaggc     840
taatgattgt attgtacaat tagtaagaat taaggacaaa ggtctctttta cctgaagttt     900 cctgggtgct tttattcatt cattcattca ttcattcatt cattcattca tttagtcaaa     960
ttagttcatt tctgatgcaa tgactgactg attactcccc agaccaatgc tccttcctgt    1020
tttaggttca cagatagcat ttcctacctt ctcttgtcct tccttttgtc caaaattttg    1080
agttctagac aaccacagaa ttgcctagaa atgctggaca gaattcatgc atctgattcc    1140
tggtaagacc gtcgatgcac tataaacttg cagaagctga cagcagactg ttcttcactt    1200
caactcattt atccctttcc tttgggttct gtccaaatca catcaccaga tcacaagaac    1260
ctaacatcag attgagacgt aaatagatga tatcacattg gatttccacc attgagccac    1320
accaccagcc acctgcctga taactttcac agtcccagaa gatattatac aagttactag    1380
ggcaaaaaga gatcaaagtc tgaatcagct gtgaacccta tgaatggcaa tacctactta    1440
tcaggcaata caagcccacc cgtgtgatag tggaataaca gtaatatggg caatcactgg    1500
attgagtcct ggccccactg cagagaatcc atgccaagca ctgtaaatcc aggaagaaaa    1560
aaaaaaacct atcactgaag aagacataaa ccctagaaag gaacttacta ctcttactta    1620
actgagtgag caaagcaaca agttatcttc taagtactta tgctggtgct catacacaaa    1680
attatccatc attcttaatt agagaattct ctctagtgaa tggttgtgga ttcaaagact    1740
cataaatacc aagggtgcta agaatgagcg acaattaaga actcagccct aaacaagatt    1800 tttataccttc atcttctaag gctcagaaac attgtggaag aaggtgtcaa agaatgtaa    1860 gagtgaaaag agtgagaagg gctgccaata tcatctttgc tatcatgaac tcacaaaagc    1920
```

```
tgcagttgtt agtgccagga ctgtgtgaca ttgtcactac caacactcag ccttgggtgg      1980
ggaggagggc ataatgtcat actcttcatc attgagccat tggttactaa cagattctag      2040
gagaatcact ctctcttgtt atgtatccat ccatgaatct acaaggctcc attgggcagt      2100
tccaaactgg aggtcagaaa aatttcactg atgaaactca ctgggacaca atcaaaaata      2160
tgaaagagct ttgtagccat ctttttttct gacaagggtg ggagaggcat aacaaggaag      2220
gtaaataatt gattgcatta tatacacata tgaaactgtc aaagaacgca atttaaaaag      2280
tacatagtaa gtggttttcc atacaattta atttattatc acacagttgt tctttacagt      2340
atgtcttgat tatctctatc cctgactccc atgtcacccc cacaaacacc ctcaatatat      2400
ctccctccac cttatcaccc cttaatttct ttcattttac tattttatag ataatccact      2460
gaattcaatt agtgctgtct gttggaaagc cgaaggagac cgatatgttg gcttgatttg      2520
acacaggtct tctgcaggtg accaagatga agtgacttga atgtgatagc catgctatga      2580
aaaagagggc ttcatgtatt gtatcaaaag ggagcgtttc tcagctcctc tctccagcct      2640
ctgtctcata ttctttctgc tccgtcttcc tctgtaacat agtaaatttg tacagaacgg      2700
tcacaagtca caaatttggt agactacatg atgaaatttg caatgacttt ggagtactta      2760
acatggattt gaatgtccat ttggcatcgt tctagaagat aagtccaaag taagtgtgct      2820
atcttaccat cttccttcct tgtaggagtc ggccacgttt cccactctag accttagctc      2880
ctctagttag ctgcttcaaa gcatcaagtg gagtccgcat aatcactttg tactaattca      2940
taagctcata aatccagaca aagtgaaagt caaatctcaa gtcctgggcc acttatttgt      3000
tttctgtgca tcggacttag gattatttgc cctcttcctg ttccactgca tcagttctgt      3060
cagtgggggg ggggggggtt gggagtgtgt gtgtgtgtgt gtgtgtgtgt gtgtgtgtgt      3120
gtgtgtgtgt tgcttacaaa gctgtcataa tgatgaaaca gagtatcagt cacatggtaa      3180
ccacatctaa gtagagaatg tgcttctaca atgtgagctt cctctcagtg tgtccatgtc      3240
atcatagagg aggcttcttt cccagtgcac atgaaggctt cagaactaag tttgaatagg      3300
actatgtgat cagccctgaa aagcctgcag tactccttgg tgctgtgctt gaaccctcct      3360
gtttctctgc gcggtctttg tagggagact atggatataa actatttggg tggtctcttt      3420
tttttcatca ggaagacaga ggtatactgt tgattctaga catgtcaggt tgaggaaatg      3480
gaccttatgc ctaattcctt cctaattcat acagagtttc agctttaaag gacagattaa      3540
tagcggtttg agatgatttc agctctgtga cctggccatt gtgctgtgtg ttagatttcc      3600
atgctggtaa gtgaaacaat tttagggctc taaaaactca cttcaggctc taagcagcac      3660
tccacctagc cagaatgggg gagatgcagc taaacagctg ctcatgtgag cagggttacc      3720
aactccagtc gacagccagg ccagcatgac tcaccagtgt gaaactgcca agaggataat      3780
ttgatctggg gctgaatgaa caggactgca gtgtctgtcc agaccaaagt gagggatcct      3840
cccttgtctg catgtgaatc cagaccacac ctactgtctt gtaggctttg cttaccccca      3900
cccctgtatc tcattatgat gctgttcaca agttgaagta gagccagcta tgagactcat      3960
tgcataatat tcacattaga aaccactctc ttcattctat ttctatcata ggatttctaa      4020
cttaacttgt tgaaggtgtg gatattgaca tctttgagaa gaagaaga                   4068
```

<210> SEQ ID NO 6
<211> LENGTH: 3949
<212> TYPE: DNA
<213> ORGANISM: Chinese hamster

<400> SEQUENCE: 6

```
gatctgtgta gctgccacaa cacttgatct cggagtgagg ccctaactcc attgatgggt    60
gtcagctctc atcagtcgca ctgttagcaa caggagatcc agctgactgc ctctcaagtt   120
atacagtgtg tgcaccagct tccaccacag cagctgctgc tgtcagtttg gaaataaagt   180
tcattcctac cttgcaggca cttt ggcatt tgctttggga ttatttgcac ctcaggaaga   240
tccatcacta gttttcatta ttctgaatgc aatggattat cagcctgtaa ataatcaagt   300
agacctcact ggatttaaac attggaagct aagctatcaa gcagatttat gaagttcaca   360
tgcttgtgca atgtgagaag ctgactttt ggagctgcag tggcagccaa ccaagcagcc    420
tgaggtttgt tcttgaaagg gagagtgtgg actaaaggaa gcctagaaag acacagaata   480
aaatcaggag ggcagatcca gttaatactg aacaccacaa gtttatttct caccactctc   540 atataccta accaaaaggt gaacatgagt tccttcatac aaagcaaaca ctctttctt     600 gctgaatttt tcaccaattt ggtaaccata ccttagattc aaattctagt tacctgttct   660
ttagggacag gtgtcagcac atctcagacc aagtctgttt ttatttagca taagacaccc   720
catgccatga tgcaatatcc tactgtagcc acacctttga cctttaggtt ttatgatttc   780
ctaaggacag ttatgaactc tctgcccttg agccaagatg gagtccagcc gtctttatgg   840
gaactagcag tgcaatgtga ttctctcatc cattgcattc gtcaaaaggc aattgtgagt   900
aaagggagga tgtagtggtt catctatttg cctgactgat atcctaacag ctcccctagt   960 tttaatttt tttttagttc ttgtgaagat gtcatggctg gtctggagct cctgggtata   1020
ctgtagccta ttttactgtc taagcctctg gggtagctgg gattgctgga tcatggtgac   1080
aggtaactca ctacccaatt ttaaagtgaa tttgtaatga aaggatgatg attgttacct   1140
acttgttagg gctaggaatt gatttcttcc caacatttta gagattttcc ctgtgtatta   1200
atggcattta tcttgcatct acaattgatg ctgttcaaag ctgcccaggc tggcctctaa   1260
ctcacagaga tgcaaatgcc tctgcctccc gagtgctggg attaaaggcg tgcaccacta   1320
atgcctggct cttttaaaa tcttttaggt tattgcttcc taagctctag tgactatggg   1380
tagatatcaa agacaataca gttttcattg gttctgtttt ggtgtgtagt ttttgttggc   1440
tactttcttc tttacacaga tttcatgtag tgcacactca tcttgagctc tctacatagc   1500
acaagaggac cttgcaggct tgattatcca gccgctaatt cctaagtgct gagtgacaag   1560
tgtgtgacac tgtgcctctc attttgttgg ttattttaga aagagtctta ctaagttgcc   1620
cagactaggc tcaaactctg aatatctccc agctttagcc tccatagtct tgcatttaca   1680
ggcagtttaa tcttgagcta acagtccctg ctgataccaa gttttattc taggtgtcca    1740 agaggaactg tagcagtgaa ctccagtcta gccaaagaca cttgaccatt gcactctgga   1800
tcttgtcttt agatatgtat tttgggggat ttcttttaa tcaacaggaa atcaaataaa    1860
cttaaaaaag aatttacgca ggcagcactg gttcaagtat ttaatctcaa caccctgtag   1920
atataggcaa aagtatctct gagcagaaag atagccaggg ttacaaagag aaaaactgtc   1980
tcaaaaatta tatatatgtg agtgagtgtg tgcgtgttag ttattttaaa ttatatgtat   2040
aaatgtacat gcatatgcaa gagcccatgg agatcaggag aaattgtgtt ctctaagagc   2100
tgtagttact ggtgggtgaa agccaccagg gttgggagag agaaatagaa ctgtagtact   2160
atgatagaac aagaagtgct cttaacctga gttatggttc tagctcaata gatacactat   2220
tcacagttat tttaaagata ctgttgttgt tgtcttttac tgtgcatttg ggtgataaaa   2280
catgatccaa cacactcaac aaatccacat ggagtttatt ggaaaaggga ataaagggag   2340
```

-continued

| | | | | |
|---|---|---|---|---|
| gggtaggtgt | taaccaatag | ggagcagaaa | tggaaagaga | gaaaacagat | gggaggcact | 2400 |
| tgcttataaa | gggaaaggaa | acagttaaga | atgaggctca | gtagttgggg | cctttgaaac | 2460 |
| catagtcact | gaactgcctt | tggccaagat | ttacatggtc | tctgtatgca | gaatcctaat | 2520 |
| tcagtcaatt | aacacatgca | ccacacagcc | atgcaaactt | tgacagtctt | tgagatgtca | 2580 |
| gcaaggaaca | atcacctgtg | aaaacagat | cccagggcaa | gggcaggtca | cctggaaaag | 2640 |
| agaagagaag | atggatccca | gagcaggag | ggaatccaag | tgttagagag | gccactaggc | 2700 |
| caggaaagga | tctctaagga | agcaacaggc | ccaggagagt | gctgatgtgg | agtgacatgt | 2760 |
| ggagatcaag | agaaaacacc | agggtgggag | gagagaaatt | ggcagctgga | tcagggccag | 2820 |
| gtcgcacaga | acctagggag | agggagaatc | caggttatca | acaattatta | ctaggcagta | 2880 |
| ctacattttc | tgtgtcctat | tatttctgta | gttacttaca | aatatttga | gttataaaaa | 2940 |
| ggaataaaga | gccgggcagt | ggtggcacat | ggcattaaca | ccagcacttg | ggagacacag | 3000 |
| gcagttgcat | ctatgtgagt | ttgaggccag | cctggtctac | agagggagtc | ccaggaccaa | 3060 |
| aagccacaga | gtaactttgt | catacaaact | gatccagtag | gcttcatctc | agatacgcag | 3120 |
| tgatggttca | acatacaaaa | atcagtaact | gtaatccacc | ataaaaataa | actttaaaaa | 3180 |
| acacttttt | attatcccctt | tacatgctta | caaagtcatt | gataagccag | gtattggggg | 3240 |
| tgcatgcctt | taatcccagt | acttgggagg | cagaggcagg | tggatcactg | tgagttcaag | 3300 |
| gccagcctga | tctccagagc | gagtgccagg | ataggcttca | agctgcacg | gagaaaccct | 3360 |
| gtcttgaaaa | accaataaat | aaataaataa | ataaatagtc | attgacaaga | aacaaacatc | 3420 |
| ataaaagtct | tggagatatt | atggatacaa | tttacataca | cacacataat | gaaggacatt | 3480 |
| tacagcaaac | ctatagacaa | catcaaatac | aatggagaga | aaaacaaag | gaattcctat | 3540 |
| aaaatctgta | acttgacaag | tttgtgaagt | ctatatctac | tcaatacagt | acttgaagtt | 3600 |
| ctagatagac | ccattaaaca | gctaaaggac | aacaaggaaa | ggaagaagta | gaagtgttgt | 3660 |
| tacttgttga | tgatatagtg | gtaccaccta | agtgacacta | aaaattcatc | aatgaagta | 3720 |
| caggtgatta | aaactttcag | caaagtgacg | ggatacaaga | gtaactaaaa | caaccattag | 3780 |
| ccctcctatg | taaaaatggc | aaacagcttg | agaatgaaat | aaaagaagca | gcagcaatca | 3840 |
| caatagcttc | aaataatata | aaatacattc | tagtaactct | aacttgttta | attaaaaaaa | 3900 |
| ctttaagtgt | ttgaagaaag | aaattgaaga | agatatgagg | cgatggaaa | | 3949 |

<210> SEQ ID NO 7
<211> LENGTH: 1128
<212> TYPE: DNA
<213> ORGANISM: Chinese hamster

<400> SEQUENCE: 7

| | | | | | |
|---|---|---|---|---|---|
| gatcaggagt | tcaaggccac | actgaggtac | acgaaattca | accagtctga | tagatataag | 60 |
| agctgggtgc | gtgtggctcg | cacctcaggt | ggagacagga | gtataaggct | ggaggaggca | 120 |
| gtatttaggc | ttattcatat | agaggatttg | taaagacagg | acctccccag | cacttccatc | 180 |
| tgaacatttg | gtacaggtaa | gaagtcccta | tagagttggc | tcctttaatt | ctcttatgtc | 240 |
| tcaacattta | cccaattatc | tgacatctca | ctcagcgttt | ttactattta | aaccaatttg | 300 |
| aagaaatgct | acagagcacc | ttttaacctc | tacaaacaca | cataaacaca | gagagagaga | 360 |
| gagagagaga | gagagagaga | gagagagaga | cagagacaga | gacagagaca | gagacagaga | 420 |
| cagagaaaca | aatgtaataa | cgaaagaagt | catgtcatga | gaaccctgag | gctgcggtcc | 480 |
| acacccatct | gtggccagga | cacagaggcc | tagaggagcc | ctgtgacaca | agcactctct | 540 |

-continued

```
acaactggcc cttgtcccgt gcagggggca gaaaggacag attttgttgt gcagaagctt      600
tatcatcagc agcatacact gggcctctct gtccttcact gtcacatgct cctagggagt      660
tcagtcggga ggtcatgtat gtgcactatg gacctgtccc acagacactc tgtcctaatg      720
cgttctgctg gggtattttg gcaatgctgc aattgagcag tgatgtttca aggtgcacta      780
gttgttcccc ccatattctc aacacaatc aatgccacat tgtaaatcaa aacattcagg       840
ctcccctgtg aattgtaagg attttattat tggaatcctg gttttagata cctggagggt      900
agggtagggc ttgcttcatc tattcaggtg tgtaggcaag tggctcccctt gagtcttatt     960 gcccagatgg attcatcaac agaatttgtt agcatctatt ttctgctgca aagagaaccc     1020
ggtgaggtat ctgaggtgtc agaggtgaag acatctcac tgagcataca tgggacacct      1080
catgggaggg actgaaacct gtctgccaga gcacctgggt ctgaccat                  1128
```

<210> SEQ ID NO 8
<211> LENGTH: 1352
<212> TYPE: DNA
<213> ORGANISM: Chinese hamster

<400> SEQUENCE: 8

```
gatctctcag cttcctgctt tttaaaagta ttttatttta tttttatacc cattgatgtt       60
ttttgtcgtg ggtgtcggat accctgaaac tggaggtttt cattttatat ttatgttaat      120
caatgttttg ccatgggtgt tgcgtcccct gaaactggag ctacagacag gtgtgagctg      180
ccatgtgggg ctgggaactg aacttgagtc ctctggaaga ggagtcagtg ctcttaacta      240
gtgagccatc tctctaggcc ctcagcttcc tgctttggct accagctgac atgcctctcc      300
caccattatg aatgccccct caggaacctc tggaactgaa aaccaaaata aacttttttaa     360 agttgctttta gttcatggca ttttatcaca acaatagaca agaaactaat acagtaatac     420
atggcttttt aaatgatttg acagattcat gtaagtatat agtgaatttg ggtcattttt      480
caccctttaa taccattgtc atcctccttc ctaaccagct gggaccctct tcctcagcag      540
gccctcttct actttcattt tttttttttt ttttgtgtg tgtgtgtgtg tgtgtgtgta       600
tgtgtgctcg cgcgtgtgct gtgtccttat gtttatttat ataaaaaata gcgcattgac      660
tctaactttt actacacctt actggttata tatgtatgtg tatgccatgg tacatgtgca      720
gagaacaaag gacaactttc cgggagtcat ttctatcctt ccactatgca tgtggtttct      780
gggatagaac tcaggtcatt agccttggca gcaagcctct taaccctctg aaccatctcc      840
ctggcctggc attttaaaat aatctttgat gcttctatca gtatcttggc cactgataat      900
ctataattat ttctctaaga ctatttgttt tccacaaaca aaatgctata agctgggaga      960
tttataaaga agagatacat ttggctcaca gctctgaaaa ctgggaagtc caaaagcatg     1020
acaccagcag ctgtcaaatg cctttctgca gtatcataag aaatcagagg acagcacatg     1080
acaagaatgt tacaaaagga caggacaagt gttccaggct tggtctatgg ttttcatcat     1140
ttaaggccgc caattccatc acaagtgttc tcttccctat gatttcatgt aattctaaag     1200
acattctaaa accccacacc caaatactat tagcacaaga cattggagat tttagtttca     1260
atcttagctt taggggagag acactcagtt cataacagta tccccaagat ttccagtatc     1320
cagtgctgtc tcaatgcaat actactcaga ag                                    1352
```

<210> SEQ ID NO 9
<211> LENGTH: 1246
<212> TYPE: DNA

<213> ORGANISM: Chinese hamster

<400> SEQUENCE: 9

```
gatctttcca ttttctggta tcttctttaa tttctttctt ttaagactca aagttcttgc      60
tagacaggtc tttcacttgt ttggttatca ttaccccaag atattttatg ttgtttggct     120
attgtaaagg atgatgtttc tctgatttat ttctcagccc atttatctcc tgtgtataat     180
agggctagtg atttttttgag ttaatcttgt atccttccac ttagctgaag gtgtttatca    240
gctgtagtag ttccctggta gagttttttg ggttacttat gtaactatca tatcatctgc     300
aaacagtaaa aatttgactt cttcctttcc aatttgtatc cccttgttct ccttttttgtt   360
gtcatattgc cccagataga acttcaagta caagcagaag tcattctctt ctgcttcatc     420
tgtgttggga tgttcaggtc ttgctggcgt agagtcccta gattctagtg gtgtcatatt     480
gttttttctg ttattgaatg cgtttttata ttgttgtctt cccatctctt cttccagtgg     540
gttcaggtgc cgtctcttcc tctcctggtg tgtatgggtc caaggttctc tttggtggat     600
gcaagagggt ctgatactct gatgggtctt atggtgggtt caggcgggtc tggggcactc     660
cctctctagg tgggggtggg aactggacta gcacagtgat gtcatcagac ttgaggttgc     720
ttggtcctca gggggcaagt tgatttgcct gcagtcccca ggacaggagt tcccagagtg     780
gacaggcaga agtcgggctc aaggcagggg ccaagctcta catgtgattt ttaaaatgag     840
agttcagatt catgtaggca gatgataagc tcagggagaa aaatgaccta tttctaaaaa      900
ctgatgacgt gaagattgag agaaaggggtg gattttttgaa aaagaatcgg tagggagcta   960
aaaaggaaaa gagaaattaa ggatgactct caggttttgg acttgaatgt tggatggatg    1020
tttgtcccat ttgtagaaag gagaacacag gtgatttaga agtctgaggt gaggatgtca   1080
cctcatgact taaagaatct gaggttttag aatcaaatct cagggaacat cattagcaga   1140
gggaccctgt tgggtcttgc cagatgctga gcttcagctg tctcctgttt tcccacattt   1200
cctgttttttc ctaacttgta tagactctgg gaaaagaagg taccag                  1246
```

<210> SEQ ID NO 10
<211> LENGTH: 447
<212> TYPE: PRT
<213> ORGANISM: Homo sapiens

<400> SEQUENCE: 10

```
Phe Thr Val Thr Val Pro Lys Asp Leu Tyr Val Val Glu Tyr Gly Ser
1               5                   10                  15

Asn Met Thr Ile Glu Cys Lys Phe Pro Val Glu Lys Gln Leu Asp Leu
            20                  25                  30

Ala Ala Leu Ile Val Tyr Trp Glu Met Glu Asp Lys Asn Ile Ile Gln
        35                  40                  45

Phe Val His Gly Glu Glu Asp Leu Lys Val Gln His Ser Ser Tyr Arg
    50                  55                  60

Gln Arg Ala Arg Leu Leu Lys Asp Gln Leu Ser Leu Gly Asn Ala Ala
65                  70                  75                  80

Leu Gln Ile Thr Asp Val Lys Leu Gln Asp Ala Gly Val Tyr Arg Cys
                85                  90                  95

Met Ile Ser Tyr Gly Gly Ala Asp Tyr Lys Arg Ile Thr Val Lys Val
            100                 105                 110

Asn Ala Pro Tyr Asn Lys Ile Asn Gln Arg Ile Leu Val Val Asp Pro
        115                 120                 125

Val Thr Ser Glu His Glu Leu Thr Cys Gln Ala Glu Gly Tyr Pro Lys
```

```
                130                 135                 140
Ala Glu Val Ile Trp Thr Ser Ser Asp His Gln Val Leu Ser Gly Lys
145                 150                 155                 160

Thr Thr Thr Thr Asn Ser Lys Arg Glu Glu Lys Leu Phe Asn Val Thr
                165                 170                 175

Ser Thr Leu Arg Ile Asn Thr Thr Thr Asn Glu Ile Phe Tyr Cys Thr
            180                 185                 190

Phe Arg Arg Leu Asp Pro Glu Glu Asn His Thr Ala Glu Leu Val Ile
                195                 200                 205

Pro Glu Leu Pro Leu Ala His Pro Pro Asn Glu Arg Thr Pro Arg Asp
210                 215                 220

Cys Gly Cys Lys Pro Cys Ile Cys Thr Val Pro Glu Val Ser Ser Val
225                 230                 235                 240

Phe Ile Phe Pro Pro Lys Pro Lys Asp Val Leu Thr Ile Thr Leu Thr
                245                 250                 255

Pro Lys Val Thr Cys Val Val Val Asp Ile Ser Lys Asp Asp Pro Glu
                260                 265                 270

Val Gln Phe Ser Trp Phe Val Asp Asp Val Glu Val His Thr Ala Gln
            275                 280                 285

Thr Gln Pro Arg Glu Glu Gln Phe Asn Ser Thr Phe Arg Ser Val Ser
290                 295                 300

Glu Leu Pro Ile Met His Gln Asp Trp Leu Asn Gly Lys Glu Phe Lys
305                 310                 315                 320

Cys Arg Val Asn Ser Ala Ala Phe Pro Ala Pro Ile Glu Lys Thr Ile
                325                 330                 335

Ser Lys Thr Lys Gly Arg Pro Lys Ala Pro Gln Val Tyr Thr Ile Pro
                340                 345                 350

Pro Pro Lys Glu Gln Met Ala Lys Asp Lys Val Ser Leu Thr Cys Met
            355                 360                 365

Ile Thr Asp Phe Phe Pro Glu Asp Ile Thr Val Glu Trp Gln Trp Asn
370                 375                 380

Gly Gln Pro Ala Glu Asn Tyr Lys Asn Thr Gln Pro Ile Met Asp Thr
385                 390                 395                 400

Asp Gly Ser Tyr Phe Val Tyr Ser Lys Leu Asn Val Gln Lys Ser Asn
                405                 410                 415

Trp Glu Ala Gly Asn Thr Phe Thr Cys Ser Val Leu His Glu Gly Leu
                420                 425                 430

His Asn His His Thr Glu Lys Ser Leu Ser His Ser Pro Gly Lys
            435                 440                 445

<210> SEQ ID NO 11
<211> LENGTH: 451
<212> TYPE: PRT
<213> ORGANISM: Artificial Sequence
<220> FEATURE:
<223> OTHER INFORMATION: Antibody heavy chain

<400> SEQUENCE: 11

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
```

```
            50                  55                  60
Glu Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Lys Val Ser Tyr Leu Ser Thr Ala Ser Ser Leu Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 12
```

<211> LENGTH: 214
<212> TYPE: PRT
<213> ORGANISM: Artificial Sequence
<220> FEATURE:
<223> OTHER INFORMATION: Antibody light chain

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 943
<212> TYPE: DNA
<213> ORGANISM: Homo sapiens

<400> SEQUENCE: 13

| | | | | | |
|---|---|---|---|---|---|
| gtaagtgccg | tgtgtggttc | ccgcgggcct | ggcctctttta | cgggttatgg | cccttgcgtg | 60 |
| ccttgaatta | cttccacgcc | cctggctgca | gtacgtgatt | cttgatcccg | agcttcgggt | 120 |
| tggaagtggg | tgggagagtt | cgaggccttg | cgcttaagga | gccccttcgc | ctcgtgcttg | 180 |
| agttgaggcc | tggcttgggc | gctggggccg | ccgcgtgcga | atctggtggc | accttcgcgc | 240 |
| ctgtctcgct | gctttcgata | agtctctagc | catttaaaat | ttttgatgac | ctgctgcgac | 300 |
| gcttttttc | tggcaagata | gtcttgtaaa | tgcgggccaa | gatctgcaca | ctggtatttc | 360 |
| ggttttggg | gccgcgggcg | gcgacggggc | ccgtgcgtcc | cagcgcacat | gttcggcgag | 420 |
| gcggggcctg | cgagcgcggc | caccgagaat | cggacggggg | tagtctcaag | ctggccggcc | 480 |
| tgctctggtg | cctggcctcg | cgccgccgtg | tatcgcccg | ccctgggcgg | caaggctggc | 540 |
| ccggtcggca | ccagttgcgt | gagcggaaag | atggccgctt | cccggccctg | ctgcaggag | 600 |
| ctcaaaatgg | aggacgcggc | gctcgggaga | gcgggcgggt | gagtcaccca | cacaaaggaa | 660 |

```
aagggccttt ccgtcctcag ccgtcgcttc atgtgactcc acggagtacc gggcgccgtc    720
caggcacctc gattagttct cgagcttttg gagtacgtcg tctttaggtt ggggggaggg    780
gttttatgcg atggagtttc cccacactga gtgggtggag actgaagtta ggccagcttg    840
gcacttgatg taattctcct tggaatttgc cttttttgag tttggatctt ggttcattct    900
caagcctcag acagtggttc aaagtttttt tcttccattt cag                      943
```

```
<210> SEQ ID NO 14
<211> LENGTH: 447
<212> TYPE: PRT
<213> ORGANISM: Artificial Sequence
<220> FEATURE:
<223> OTHER INFORMATION: Antibody heavy chain

<400> SEQUENCE: 14
```

Gln Val Gln Leu Val Gln Ser Gly Val Glu Val Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys

```
                305                 310                 315                 320
Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 15
<211> LENGTH: 218
<212> TYPE: PRT
<213> ORGANISM: Artificial Sequence
<220> FEATURE:
<223> OTHER INFORMATION: Antibody light chain

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
210                 215
```

<210> SEQ ID NO 16
<211> LENGTH: 680
<212> TYPE: DNA
<213> ORGANISM: human cytomegalovirus

<400> SEQUENCE: 16

| | | | | | |
|---|---|---|---|---|---|
| gttgacattg | attattgact | agttattaat | agtaatcaat | tacggggtca | ttagttcata | 60 |
| gcccatatat | ggagttccgc | gttacataac | ttacggtaaa | tggcccgcct | ggctgaccgc | 120 |
| ccaacgaccc | ccgcccattg | acgtcaataa | tgacgtatgt | tcccatagta | acgccaatag | 180 |
| ggactttcca | ttgacgtcaa | tgggtggagt | atttacggta | aactgcccac | ttggcagtac | 240 |
| atcaagtgta | tcatatgcca | agtacgcccc | ctattgacgt | caatgacggt | aaatggcccg | 300 |
| cctggcatta | tgcccagtac | atgaccttat | gggactttcc | tacttggcag | tacatctacg | 360 |
| tattagtcat | cgctattacc | atggtgatgc | ggttttggca | gtacatcaat | gggcgtggat | 420 |
| agcggtttga | ctcacgggga | tttccaagtc | tccaccccat | tgacgtcaat | gggagtttgt | 480 |
| tttggcacca | aaatcaacgg | gactttccaa | aatgtcgtaa | caactccgcc | ccattgacgc | 540 |
| aaatgggcgg | taggcgtgta | cggtgggagg | tctatataag | cagagctcgt | ttagtgaacc | 600 |
| gtcagatcgc | ctggagacgc | catccacgct | gttttgacct | ccatagaaga | caccgggacc | 660 |
| gatccagcct | ccggactcta | | | | | 680 |

<210> SEQ ID NO 17
<211> LENGTH: 3619
<212> TYPE: DNA
<213> ORGANISM: Chinese hamster

<400> SEQUENCE: 17

| | | | | | |
|---|---|---|---|---|---|
| ttaattaccg | acaatggctg | gtacagcaag | tagcacggaa | aaaaagtgaa | acagttgcac | 60 |
| tgttcatggt | tggcaataat | tcttcaggaa | aatatttact | atcaatcagt | tatgagaaaa | 120 |
| gggactctgt | gctcgtaaaa | cagcacgttg | cttctcatac | caggaccatt | ttgcttcagc | 180 |
| ataatctgaa | tttaaacagc | ttgtttcctg | cggatataat | tttggaaata | aataaaacaa | 240 |
| gtcttctatc | aaaatccgga | gtgagtggga | aggaacatca | catctttcta | tctcagtcag | 300 |
| tttcaaacag | attattagtc | ccaagtaaaa | aacagtaata | acaaacaaca | aaaatacaga | 360 |
| atgtacacaa | ggccactgat | gggcttattc | caaagaaaga | cagaccttc | ccactgtagg | 420 |
| ccaggtatca | aggtagaagt | gcccgaacaa | ttcaatttta | actgcacatg | tttatggaag | 480 |
| gggtgtgagg | tgtaagggta | aattatggaa | aagcctcaaa | ccaaaatttt | ctgtagtatt | 540 |
| tcaataaagt | caataacaag | ataacataaa | aattaatgtt | ctcagttttt | ttcataatta | 600 |
| aaaaacatga | aggttgacaa | ttaggtacaa | tgtgattata | gattttaaag | actaagctga | 660 |
| cagtcaataa | ccgctgtcca | tttaaagcta | caataaaat | agagctcatc | atgttcccca | 720 |
| aacaaatccc | ataaagcacc | agggctgtga | gcagcagatg | agatgctcta | aaaagcaaac | 780 |
| tagctggcat | ggtggtgcat | ccagcacttg | ggaggcggag | gcaggtggat | ttctgtgagt | 840 |
| tcaaggacag | cctggttgat | atggccaaag | ctacatcgga | cagacagaca | gacaaaacaa | 900 |
| aacaaaaaag | caaactatat | tcaagatatt | tcatggcttc | aaatactact | tggacccctc | 960 |
| cccatttta | ttttaaatg | tttctttctt | gaactctttc | tttcaggaga | ctgctgtcag | 1020 |
| cctaaggtag | cttatgaagc | agctgtgctt | ccttacagga | actgaatagt | tacagggcaa | 1080 |
| ccagcagagg | aaaactacac | acaaaatact | acaggtttca | tctctgcttt | tgagaaggac | 1140 |
| caatgtcttc | tgtaaaatgc | aaacaagtaa | taattaaaag | gtctaagact | acaattagta | 1200 |

```
ttgatacccaaaccaaaattactctgactgaaattcagttgctttgaaccataagggga    1260
aaaaaaggctggcttcactgtatttcagtggcgttacatggagacagctggacatgtagg    1320
ccacaatggagaccagtttgaatcagtatcagacgccagtttctgaaggaaagtcctcac    1380
agccacgtcagtgtagcagacaaaactactgttaagaactaaaggtgaagaacaagaact    1440
agagaaatgcttacagaactacaaaaatatctttgagtcatttcttttaaaggtcaagca    1500
gtaaatgaggccaggagagacagtatgaaatcatgagacagatataacatgtttagcaat    1560
aagaaaggaaaactctcattgttgccatgctagaggaggccactgcaataaacatttttt    1620
tcagttacgtattttatttgatgatttggctcaaatctgaagcaatgaactagaagaca    1680
ggatgtgggccaataaaaggaaccaggaagctggttgtgttccaaatggaaattacagaa    1740
atcattattcaattagagtggttaaggggacaatgaaagaaaataggtgtcagaataatg    1800
ttaaaacaagcaagaatgggacgagaaggtcaccatctgggagcaagtgaaacagactga    1860
tgagcagcaatgagcaaacttatttcctcacccaagagcatggaaggaatatataccaccg    1920
tgccagacgccacaagatttctaaccgtgcaccactgaagtagagggtagaaaaaagaaa    1980
aaagaacagcaaaaacaaatccaccccacactatacacacagcaacaaggctaaggagtg    2040
tagaaacactggcttaccacgtacaggaaaacaaaggaacagatgctcagttggccagc    2100
tctcaatgaaactcattaaaattgtcgccctgtccttggattggtggtcatgcgaaattt    2160
gtgccttgttagccagaagtaacttgtgatgaaggagaaacagcatgtccaaacaaga    2220
attgaaacacttgttgatctatactcaatgctagatataaaacaggatcaagtagcactt    2280
acaaactgttactaagtaattgaaaattaaatgtaacttacactactcctctttttttt    2340
tgtagcaaattaagatgtgaacttaaggcacaatttgatgaacctaccattgcagctac    2400
aatataaaataaattcttacatttctcataggctaagtccaatgccacaagctgtatg    2460
tttgcagtaataaagcaaggtcaggaactgccatgtatttgggaaatataataaaaatt    2520
attgttgctcctatgtcctgattgatcatgtccctccctaaccacctaatgtgtaagaac    2580
agagtctccatgaacagaatatagagcactatgcaataagtaaatgaatgaacagattaat    2640
aagagatcccagagggcttagctcatccctccatcctgagattatattatagcaaggat    2700
tccatctatgaagaagagtcaacttccaactagacattgaatctactgtcaccatgatct    2760
tcccatatctagaactataaaaataagtcactgtttataagctaccttgtttattttgg    2820
ttgtaataacacaaagaaattagctcttcttgagatttataacaaagatggagttgaca    2880
tgacatcaagtcctatctctaataatgacagtaaatagggcctatataggacacaagag    2940
atgaagcagaaagttggaaaagttgtaaaacagtcacccccaaaatggtaataaaggtt    3000
attttttgcctaaaaataaagacaaactctagaaatacaactcatactgaacgttatcctc    3060
aagacagtaaagttaacaaaaagttatccccagtcaatctagaaaattgaaagaaaaaa    3120
attaagatttctaattaaatttttgtgtatgggtgttttgtctatatgtatgtctgtaga    3180
ggccagaagaagacactgggtcctctggaacgggagctgcagatggttgagagccgtcat    3240
acggtgctgacaggtaacccgggtcctatacaggagcagcccttaaccaatgagctctta    3300
accaatgaaccctctccagccctgaagattttcaattttaatattttgtatctagaa    3360
atataacacacatttatacataaaagactaggctcatatgtcagctaaatacatgtttcc    3420
actcaaaatcaccaagtaagacatttctcaagaaagaaggcacaacctaagctgggacc    3480
tctgcagcagtctcacgcatgtggctcacactgtcaccagcagggtatttctggcgtgct    3540
acacctgcacttaaaggaggccaggcatggcggtgctggcctttaatcccagcactcacg    3600
```

| gggcagaggc aggcagatc | 3619 |

<210> SEQ ID NO 18
<211> LENGTH: 1114
<212> TYPE: DNA
<213> ORGANISM: Chinese hamster

<400> SEQUENCE: 18

| tccacactca tgttgacatt aaagccatcg acaatctcag taagtactag taaacaagta | 60 |
| acaaataaga ctgatccatc acacaacatt accctggctg tgtctttgga gtaaaaatca | 120 |
| tgtagatcaa ggtatggtat gcttgaacac caaaaagtaa ccacagagta aagagtaga | 180 |
| gtccagtgag tgccttatgc gtgagcccac ttcccttttt gcgtttgttt ttacttaatg | 240 |
| tctggcagaa ttcaggcatg taggtcagag gccaccttgc aggagtccgt tctctctttc | 300 |
| caccaactgg atcccaggga caggacacag gtcttgggct tggcagcggg tgcccttacc | 360 |
| tactgagcca tttcaccact gacttggttt tactgaaagc taactctgaa gactggaatt | 420 |
| cgatactttt ttagggtgat gagtcactca ctgtacagcc tcagcactat tgctgaagta | 480 |
| cattaccctc acaaaccagg cagccggaga ctcactgctt acatgtaatc gaggccatgc | 540 |
| tatgttaggt aacatgttgg agacttacca aaaactgtgt tttaaagtta cttgcaacct | 600 |
| ttctgtaacc acgcaaactg ctgtgtgatt ctttaaccta tgtctccaca atcacaacag | 660 |
| acatctgttc cgggtaattg cacatttcta attaaagctt tcaaagtggg ccaggttctc | 720 |
| tggagctgaa atgttcgttg aaggggggcaa agttatttc tctaacatca tgagggaact | 780 |
| gggtcagggt gtgggactg caccctgctg aggggatggt ataggaatga cccacctttg | 840 |
| gcctgtgttc cttttgtttt gctttgtgca tgtgtttgca tttctgtttg catgcaagtg | 900 |
| agctcatttg ctgtggaagc ccaaagctga tgtcactctc tatcttattc actgaaccag | 960 |
| agtcgctcca cgaacccaga gctctcagct aacactagcc tagctagcca gctgcccttg | 1020 |
| ggatcctttc tcagccttcc aagtgctgaa attgcaggta cactactaag cccgtaggcc | 1080 |
| tttgtgtggg ttctgcagat ccaaacttca gatc | 1114 |

<210> SEQ ID NO 19
<211> LENGTH: 4068
<212> TYPE: DNA
<213> ORGANISM: Chinese hamster

<400> SEQUENCE: 19

| tcttcttctt ctcaaagatg tcaatatcca caccttcaac aagttaagtt agaaatccta | 60 |
| tgatagaaat agaatgaaga gagtggtttc taatgtgaat attatgcaat gagtctcata | 120 |
| gctggctcta cttcaacttg tgaacagcat cataatgaga tacaggggtg ggggtaagca | 180 |
| aagcctacaa gacagtaggt gtggtctgga ttcacatgca gacaagggag gatccctcac | 240 |
| tttggtctgg acagacactg cagtcctgtt cattcagccc cagatcaaat tatcctcttg | 300 |
| gcagtttcac actggtgagt catgctggcc tggctgtcga ctggagttgg taaccctgct | 360 |
| cacatgagca gctgtttagc tgcatctccc ccattctggc taggtggagt gctgcttaga | 420 |
| gcctgaagtg agtttttaga gccctaaaat tgtttcactt accagcatgg aaatctaaca | 480 |
| cacagcacaa tggccaggtc acagagctga atcatctca aaccgctatt aatctgtcct | 540 |
| ttaaagctga aactctgtat gaattaggaa ggaattaggc ataaggtcca tttcctcaac | 600 |
| ctgacatgtc tagaatcaac agtataccte tgtcttcctg atgaaaaaaa agagaccacc | 660 |

```
caaatagttt atatccatag tctccctaca aagaccgcgc agagaaacag gagggttcaa      720
gcacagcacc aaggagtact gcaggctttt cagggctgat cacatagtcc tattcaaact      780
tagttctgaa gccttcatgt gcactgggaa agaagcctcc tctatgatga catggacaca      840
ctgagaggaa gctcacattg tagaagcaca ttctctactt agatgtggtt accatgtgac      900
tgatactctg tttcatcatt atgacagctt tgtaagcaac acacacacac acacacacac      960
acacacacac acacacacac acactcccaa cccccccccc ccccactgac agaactgatg     1020
cagtggaaca ggaagagggc aaataatcct aagtccgatg cacagaaaac aaataagtgg     1080
cccaggactt gagatttgac tttcactttg tctggattta tgagcttatg aattagtaca     1140
aagtgattat gcggactcca cttgatgctt tgaagcagct aactagagga gctaaggtct     1200
agagtgggaa acgtggccga ctcctacaag gaaggaagat ggtaagatag cacacttact     1260
ttggacttat cttctagaac gatgccaaat ggacattcaa atccatgtta agtactccaa     1320
agtcattgca aatttcatca tgtagtctac caaatttgtg acttgtgacc gttctgtaca     1380
aatttactat gttacagagg aagacggagc agaaagaata tgagacagag gctggagaga     1440
ggagctgaga aacgctccct tttgataaca tacatgaagc cctcttttttc atagcatggc     1500 tatcacattc aagtcacttc atcttggtca cctgcagaag acctgtgtca aatcaagcca     1560
acatatcggt ctccttcggc tttccaacag acagcactaa ttgaattcag tggattatct     1620
ataaaatagt aaaatgaaag aaattaaggg gtgataaggt ggagggagat atattgaggg     1680
tgtttgtggg ggtgacatgg gagtcaggga tagagataat caagacatac tgtaaagaac     1740
aactgtgtga taataaatta aattgtatgg aaaaccactt actatgtact ttttaaattg     1800
cgttctttga cagtttcata tgtgtatata atgcaatcaa ttatttaccct tccttgttat     1860 gcctctccca cccttgtcag aaaaaaagat ggctacaaag ctctttcata tttttgattg     1920
tgtcccagtg agtttcatca gtgaaatttt tctgacctcc agtttggaac tgcccaatgg     1980
agccttgtag attcatggat ggatacataa caagagagag tgattctcct agaatctgtt     2040
agtaaccaat ggctcaatga tgaagagtat gacattatgc cctcctcccc acccaaggct     2100
gagtgttggt agtgacaatg tcacacagtc ctggcactaa caactgcagc ttttgtgagt     2160
tcatgatagc aaagatgata ttggcagccc ttctcactct tttcactctt acattctttt     2220
gacaccttct tccacaatgt ttctgagcct tagaagatga ggtataaaaa tcttgtttag     2280
ggctgagttc ttaattgtcg ctcattctta gcacccttgg tatttatgag tctttgaatc     2340
cacaaccatt cactagagag aattctctaa ttaagaatga tggataattt tgtgtatgag     2400
caccagcata agtacttaga agataacttg ttgctttgct cactcagtta agtaagagta     2460
gtaagttcct ttctagggtt tatgtcttct tcagtgatag gttttttttt ttcttcctgg     2520
atttacagtg cttggcatgg attctctgca gtggggccag gactcaatcc agtgattgcc     2580
catattactg ttattccact atcacacggg tgggcttgta ttgcctgata agtaggtatt     2640
gccattcata gggttcacag ctgattcaga ctttgatctc ttttttgccct agtaacttgt     2700 ataatatctt ctgggactgt gaaagttatc aggcaggtgg ctggtggtgt ggctcaatgg     2760
tggaaatcca atgtgatatc atctatttac gtctcaatct gatgttaggt tcttgtgatc     2820
tggtgatgtg atttggacag aacccaaagg aaagggataa atgagttgaa gtgaagaaca     2880
gtctgctgtc agcttctgca agtttatagt gcatcgacgg tcttaccagg aatcagatgc     2940
atgaattctg tccagcattt ctaggcaatt ctgtggttgt ctagaactca aaattttgga     3000
caaaaggaag gacaagagaa ggtaggaaat gctatctgtg aacctaaaac aggaaggagc     3060
```

```
attggtctgg ggagtaatca gtcagtcatt gcatcagaaa tgaactaatt tgactaaatg    3120
aatgaatgaa tgaatgaatg aatgaatgaa tgaataaaag cacccaggaa acttcaggta    3180
aagagacctt tgtccttaat tcttactaat tgtacaatac aatcattagc ctttaacaca    3240
aactcggctc ttaggtattt tttttatttt tattttttag aaagacaaag tgacatatgt    3300
ataaaattgt tttaaaaatg caaaggattt ctagtcattc ttgtaattag cttggtctct    3360
cagatgctgc agggttattc tcctacaact gcaaacagaa gaattaaaaa tacagaaaaa    3420
attcagaatc aattttcatt atgggcttgg actgggaaaa atgtgaaata attcttacaa    3480
gaccatgttc ccatggttga aaactttat cagcaatatg ccaattacga catacgtgaa    3540
aagtgaataa attgtctcct actaccttac caccaaggaa atatgtttcc aagtcatgca    3600
tacaaaagag aatttcacaa tgagtaagga caggaggaag gaaaggagat taaatatgaa    3660
gaggaaaaga ctaggaattc tgtgagaact tttaccatta actttagcat actgtaatat    3720
ggaacagtaa cgaaattata gtggagagaa acaaaagttc tacaaaagtc tataagatga    3780
atgaacttac attgtcagta attgacagca agttgaaacc tgagtcagaa tccaatctca    3840
ttcttgctcg catgtctcga ccctgccttg ctgatgctgt ttagtgactt aagaaattaa    3900
aagaatattt gtagtaaaat gagactcaga atcctagcct ctgtccaact attagaagcc    3960
aacaggtcag ctgtgtcctt ttctaacaga tgagaaaact gagccccaga ggagagatgt    4020
ttcgcccagc atcagagcct ttcaactcag agccagacct agaagatc                 4068

<210> SEQ ID NO 20
<211> LENGTH: 3949
<212> TYPE: DNA
<213> ORGANISM: Chinese hamster

<400> SEQUENCE: 20
tttccatcgc ctcatatctt cttcaatttc tttcttcaaa cacttaaagt ttttttaatt      60
aaacaagtta gagttactag aatgtatttt atattatttg aagctattgt gattgctgct     120
gcttctttta tttcattctc aagctgtttg ccatttttac ataggagggc taatggttgt     180
tttagttact cttgtatccc gtcactttgc tgaaagtttt aatcacctgt acttccattg     240
atgaattttt agtgtcactt aggtggtacc actatatcat caacaagtaa caacacttct     300
acttcttcct ttccttgttg tcctttagct gtttaatggg tctatctaga acttcaagta     360
ctgtattgag tagatataga cttcacaaac ttgtcaagtt acagatttta taggaattcc     420 tttgttttt ctctccattg tatttgatgt tgtctatagg tttgctgtaa atgtccttca     480
ttatgtgtgt gtatgtaaat tgtatccata atatctccaa gacttttatg atgtttgttt     540
cttgtcaatg actatttatt tatttattta tttattggtt tttcaagaca gggtttctcc     600
gtgcagcttt gaagcctatc ctggcactcg ctctggagat caggctggcc ttgaactcac     660
agtgatccac ctgcctctgc ctcccaagta ctgggattaa aggcatgcac ccccaatacc     720
tggcttatca atgactttgt aagcatgtaa agggataata aaaagtgtt ttttaaagtt     780 tattttatg gtggattaca gttactgatt tttgtatgtt gaaccatcac tgcgtatctg     840
agatgaagcc tactgatca gttgtatga caaagttact ctgtggcttt tggtcctggg     900
actccctctg tagaccaggc tggcctcaaa ctcacataga tgcaactgcc tgtgtctccc     960
aagtgctggt gttaatgcca tgtgccacca ctgcccggct cttattcct ttttataact    1020 caaatatttt gtaagtaact acagaaataa taggacacag aaaatgtagt actgcctagt    1080
```

```
aataattgtt gataacctgg attctccctc tccctaggtt ctgtgcgacc tggccctgat    1140
ccagctgcca atttctctcc tcccaccctg gtgttttctc ttgatctcca catgtcactc    1200
cacatcagca ctctcctggg cctgttgctt ccttagagat cctttcctgg cctagtggcc    1260
tctctaacac ttggattccc tccctgctct gggatccatc ttctcttctc ttttccaggt    1320
gacctgccct tgccctggga tctgtttttc acaggtgatt gttccttgct gacatctcaa    1380
agactgtcaa agtttgcatg gctgtgtggt gcatgtgtta attgactgaa ttaggattct    1440
gcatacagag accatgtaaa tcttggccaa aggcagttca gtgactatgg tttcaaaggc    1500
cccaactact gagcctcatt cttaactgtt tcctttccct ttataagcaa gtgcctccca    1560
tctgttttct ctcttttccat ttctgctccc tattggttaa cacctacccc tccctttatt    1620
cccttttcca ataaactcca tgtggatttg ttgagtgtgt tggatcatgt tttatcaccc    1680
aaatgcacag taaaagacaa caacaacagt atctttaaaa taactgtgaa tagtgtatct    1740
attgagctag aaccataact caggttaaga gcacttcttg ttctatcata gtactacagt    1800
tctatttctc tctcccaacc ctggtggctt tcacccacca gtaactacag ctcttagaga    1860
acacaatttc tcctgatctc catgggctct gcatatgca tgtacattta tacatataat    1920
ttaaaataac taacacgcac acactcactc acatatatat aattttttgag acagtttttc    1980 tctttgtaac cctggctatc tttctgctca gagatacttt tgcctatatc tacagggtgt    2040
tgagattaaa tacttgaacc agtgctgcct gcgtaaattc ttttttaagt ttatttgatt    2100
tcctgttgat taaaagaaa tcccccaaaa tacatatcta aagacaagat ccagagtgca    2160
atggtcaagt gtctttggct agactggagt tcactgctac agttcctctt ggacacctag    2220
aataaaaact tggtatcagc agggactgtt agctcaagat taaactgcct gtaaatgcaa    2280
gactatggag gctaaagctg ggagatattc agagtttgag cctagtctgg gcaacttagt    2340
aagactcttt ctaaaataac caacaaaatg agaggcacag tgtcacacac ttgtcactca    2400
gcacttagga attagcggct ggataatcaa gcctgcaagg tcctcttgtg ctatgtagag    2460
agctcaagat gagtgtgcac tacatgaaat ctgtgtaaag aagaaagtag ccaacaaaaa    2520
ctacacacca aaacagaacc aatgaaaact gtattgtctt tgatatctac ccatagtcac    2580
tagagcttag gaagcaataa cctaaaagat tttaaaaaga gccaggcatt agtggtgcac    2640
gcctttaatc ccagcactcg ggaggcagag gcatttgcat ctctgtgagt tagaggccag    2700
cctgggcagc tttgaacagc atcaattgta gatgcaagat aaatgccatt aatacacagg    2760
gaaaatctct aaaatgttgg gaagaaatca attcctagcc ctaacaagta ggtaacaatc    2820
atcatccttt cattacaaat tcactttaaa attgggtagt gagttacctg tcaccatgat    2880
ccagcaatcc cagctacccc agaggcttag acagtaaaat aggctacagt atacccagga    2940
gctccagacc agccatgaca tcttcacaag aactaaaaaa aaattaaaaa ctaggggagc    3000
tgttaggata tcagtcaggc aaatagatga accactacat cctccctta ctcacaattg    3060 ccttttgacg aatgcaatgg atgagagaat cacattgcac tgctagttcc cataaagacg    3120
gctggactcc atcttggctc aagggcagag agttcataac tgtccttagg aaatcataaa    3180
acctaaaggt caaggtgtg gctacagtag gatattgcat catggcatgg ggtgtcttat    3240
gctaaataaa aacagacttg gtctgagatg tgctgacacc tgtccctaaa gaacaggtaa    3300
ctagaatttg aatctaaggt atggttacca aattggtgaa aaattcagca agaaaagagt    3360
gtttgctttg tatgaaggaa ctcatgttca ccttttggtt aaggtatatg agagtggtga    3420
gaaataaact tgtggtgttc agtattaact ggatctgccc tcctgatttt attctgtgtc    3480
```

```
tttctaggct tcctttagtc cacactctcc ctttcaagaa caaacctcag gctgcttggt    3540
tggctgccac tgcagctcca aaaagtcagc ttctcacatt gcacaagcat gtgaacttca    3600
taaatctgct tgatagctta gcttccaatg tttaaatcca gtgaggtcta cttgattatt    3660
tacaggctga taatccattg cattcagaat aatgaaaact agtgatggat cttcctgagg    3720
tgcaaataat cccaaagcaa atgccaaagt gcctgcaagg taggaatgaa ctttatttcc    3780
aaactgacag cagcagctgc tgtggtggaa gctggtgcac acactgtata acttgagagg    3840
cagtcagctg gatctcctgt tgctaacagt gcgactgatg agagctgaca cccatcaatg    3900
gagttagggc ctcactccga gatcaagtgt tgtggcagct acacagatc                3949
```

<210> SEQ ID NO 21
<211> LENGTH: 1128
<212> TYPE: DNA
<213> ORGANISM: Chinese hamster

<400> SEQUENCE: 21

```
atggtcagac ccaggtgctc tggcagacag gtttcagtcc ctcccatgag gtgtcccatg     60
tatgctcagt gagatgtcct tcacctctga cacctcagat acctcaccgg gttctctttg    120
cagcagaaaa tagatgctaa caaattctgt tgatgaatcc atctgggcaa taagactcaa    180
gggagccact tgcctacaca cctgaataga tgaagcaagc cctaccctac cctccaggta    240
tctaaaacca ggattccaat aataaaatcc ttacaattca caggggagcc tgaatgtttt    300
gatttacaat gtggcattga ttgtgttgga gaatatgggg ggaacaacta gtgcaccttg    360
aaacatcact gctcaattgc agcattgcca aaataccca gcagaacgca ttaggacaga    420
gtgtctgtgg gacaggtcca tagtgcacat acatgacctc ccgactgaac tccctaggag    480
catgtgacag tgaaggacag agaggcccag tgtatgctgc tgatgataaa gcttctgcac    540
aacaaaatct gtccttttctg cccccttgcac gggacaaggg ccagttgtag agagtgcttg    600
tgtcacaggg ctcctctagg cctctgtgtc ctggccacag atgggtgtgg accgcagcct    660
cagggttctc atgacatgac ttctttcgtt attacatttg tttctctgtc tctgtctctg    720
tctctgtctc tgtctctgtc tctctctctc tctctctctc tctctctctg    780
tgtttatgtg tgtttgtaga ggttaaaagg tgctctgtag catttcttca aattggttta    840
aatagtaaaa acgctgagtg agatgtcaga taattgggta aatgttgaga cataagagaa    900
ttaaaggagc caactctata gggacttctt acctgtacca aatgttcaga tggaagtgct    960
ggggaggtcc tgtctttaca aatcctctat atgaataagc ctaaatactg cctcctccag   1020
ccttatactc ctgtctccac ctgaggtgcg agccacacgc acccagctct tatatctatc   1080
agactggttg aattttcgtgt acctcagtgt ggccttgaac tcctgatc                1128
```

<210> SEQ ID NO 22
<211> LENGTH: 1352
<212> TYPE: DNA
<213> ORGANISM: Chinese hamster

<400> SEQUENCE: 22

```
cttctgagta gtattgcatt gagacagcac tggatactgg aaatcttggg gatactgtta     60
tgaactgagt gtctctcccc taaagctaag attgaaacta aatctccaa tgtcttgtgc    120 taatagtatt tgggtgtggg gttttagaat gtctttagaa ttacatgaaa tcataggaa    180 gagaacactt gtgatggaat tggcggcctt aaatgatgaa aaccatagac caagcctgga   240
```

```
acacttgtcc tgtccttttg taacattctt gtcatgtgct gtcctctgat ttcttatgat    300
actgcagaaa ggcatttgac agctgctggt gtcatgcttt tggacttccc agtttccaga    360
gctgtgagcc aaatgtatct cttctttata aatctcccag cttatagcat tttgtttgtg    420
gaaaacaaat agtcttagag aaataattat agattatcag tggccaagat actgatagaa    480
gcatcaaaga ttattttaaa atgccaggcc agggagatgg ttcagagggt taagaggctt    540
gctgccaagg ctaatgacct gagttctatc ccagaaacca catgcatagt ggaaggatag    600
aaatgactcc cggaaagttg tcctttgttc tctgcacatg taccatggca tacacataca    660
tatataacca gtaaggtgta gtaaaagtta gagtcaatgc ctatttttt atataaataa     720 acataaggac acagcacacg cgcgagcaca catacacaca cacacacaca cacacacaaa    780
aaaaaaaaaa aaaaatgaaa gtagaagagg gcctgctgag gaagagggtc ccagctggtt    840
aggaaggagg atgacaatgg tattaaaggg tgaaaaatga cccaaattca ctatatactt    900
acatgaatct gtcaaatcat ttaaaaagcc atgtattact gtattagttt cttgtctatt    960
gttgtgataa aatgccatga actaaagcaa cctttaaaaag tttattttgg ttttcagttc   1020
cagaggttcc tgagggggca ttcataatgg tgggagaggc atgtcagctg gtagccaaag   1080
caggaagctg agggcctaga gagatggctc actagttaag agcactgact cctcttccag   1140
aggactcaag ttcagttccc agccccacat ggcagctcac acctgtctgt agctccagtt   1200
tcaggggacg caacacccat ggcaaaacat tgattaacaa aaatataaaa tgaaaacctc   1260
cagtttcagg gtatccgaca cccacgacaa aaaacatcaa tgggtataaa aataaaataa   1320 aatacttttta aaaagcagga agctgagaga tc                                1352

<210> SEQ ID NO 23
<211> LENGTH: 1246
<212> TYPE: DNA
<213> ORGANISM: Chinese hamster

<400> SEQUENCE: 23
ctggtacctt cttttcccag agtctataca agttaggaaa aacaggaaat gtgggaaaac     60
aggagacagc tgaagctcag catctggcaa gacccaacag ggtccctctg ctaatgatgt    120
tccctgagat ttgattctaa aacctcagat tctttaagtc atgaggtgac atcctcacct    180
cagacttcta aatcacctgt gttctccttt ctacaaatgg gacaaacatc catccaacat    240
tcaagtccaa aacctgagag tcatccttaa tttctctttt ccttttagc tccctaccga     300 ttctttttca aaaatccacc cttttctctca atcttcacgt catcagtttt tagaaatagg    360
tcatttctct ccctgagctt atcatctgcc tacatgaatc tgaactctca ttttaaaaat    420
cacatgtaga gcttggcccc tgccttgagc ccgacttctg cctgtccact ctgggaactc    480
ctgtcctggg gactgcaggc aaatcaactt gccccctgag gaccaagcaa cctcaagtct    540
gatgacatca ctgtgctagt ccagttccca cccccaccta gagagggagt gcccagacc    600 cgcctgaacc caccataaga cccatcagag tatcagaccc tcttgcatcc accaaagaga    660
accttggacc catacacacc aggagaggaa gagacggcac ctgaacccac tggaagaaga   720
gatgggaaga caacaatata aaaacgcatt caataacaga aaaacaata tgacaccact    780 agaatctagg gactctacgc cagcaagacc tgaacatccc aacacagatg aagcagaaga   840
gaatgacttc tgcttgtact tgaagttcta tctgggcaa tatgacaaca aaaaggagaa   900
caaggggata caaattggaa aggaagaagt caaattttta ctgtttgcag atgatatgat    960
agttacataa gtaacccaaa aaactctacc agggaactac tacagctgat aaacaccttc   1020
```

| | | | | | |
|---|---|---|---|---|---|
| agctaagtgg | aaggatacaa | gattaactca | aaaaatcact | agccctatta | tacacaggag | 1080
| ataaatgggc | tgagaaataa | atcagagaaa | catcatcctt | tacaatagcc | aaacaacata | 1140
| aaatatcttg | gggtaatgat | aaccaaacaa | gtgaaagacc | tgtctagcaa | gaactttgag | 1200
| tcttaaaaga | aagaaattaa | agaagatacc | agaaaatgga | aagatc | | 1246

TRANSCRIPTIONAL REGULATORY ELEMENT AND ITS USE IN ENHANCING THE EXPRESSION OF HETEROLOGOUS PROTEIN

This application is a National Stage Application under 35 U.S.C. § 371 and claims the benefit of International Application No. PCT/CN2019/100549, filed Aug. 14, 2019, which claims priority under 35 U.S.C. § 365(b) to International Application No. PCT/CN2018/100467, filed Aug. 14, 2018, the disclosure of the foregoing is incorporated herein by reference.

TECHNICAL FIELD

The present disclosure relates to the fields of molecular biology and bioengineering. In particular, the present disclosure relates to a novel transcriptional regulatory element which uses mammalian cells to express a heterologous protein. Specifically, the present disclosure relates to a transcriptional regulatory element WXRE (WuXi Regulatory Element) which is used in a eukaryotic cell line to prepare heterologous protein and enhance the expression level of the above-mentioned protein, and an expression system of the heterologous protein comprising WXRE, as well as the use of the above-mentioned expression system in producing heterologous protein.

BACKGROUND

In biological studies, the study of the proteins has received more and more attention, and the most important thing for the protein research is the selection of a protein expression system. The protein expression system refers to a molecular biological technology which uses model organisms such as bacteria, yeast, plant cells or animal cells to express heterologous proteins. The common protein expression systems are divided into prokaryotic expression systems and eukaryotic expression systems.

Among them, the prokaryotic expression system is a system which obtains heterologous proteins by prokaryotes and mainly includes *Escherichia coli* expression system, *Bacillus subtilis* expression system, Streptomycin expression system, and the like. Among them, the *Escherichia coli* expression system is the most widely used. The characteristics of the prokaryotic expression system are rapid growth of the host bacteria, easy cultivation, convenient operation, low price, clear genetic background, safe genes and high protein expression level. However, the prokaryotic expression system may not regulate the expression time and the expression level; meanwhile, the expression products of the prokaryotic expression system may exist in the form of an inclusion body with low biological activity, and the post-translational processing and modifying system is imperfect (for example, glycosylation modification may not be performed).

On the other hand, the eukaryotic expression system mainly includes the expression systems of mammalian cells, yeast cells and insect cells, which are commonly used methods to express heterologous proteins in recent years. It supplements some functions which are deficient in the prokaryotic expression systems. For example, stable disulfide bonds can be formed with the eukaryotic expression system, and after a protein is translated, the protein can be correctly modified, which enables the expressed protein to have more natural activity instead of being degraded or forming inclusion bodies. Among them, a mammalian expression system has the characteristics of being capable of inducing the highly efficient expression, performing correct folding of the expressed proteins and performing complex glycosylation modification accurately, having protein activity which is close to that of the natural protein, having no need to remove the endotoxins, and the like. Meanwhile, the mammalian expression system is the only system that can express complex proteins. As for the production of antibodies such as the humanized monoclonal antibodies, said mammalian expression system has the characteristics of being able to be produced in large amount, good humanization and the like. The host cells commonly used in the mammalian expression systems include CHO cells, COS cells, BHK cells and the like.

Adalimumab (trade name: Humira) is an anti-human tumor necrosis factor (TNF) humanized monoclonal antibody, which is approved by NMPA (National Medical Products Administration) for the treatment of rheumatoid arthritis and ankylosing spondylitis and has good therapeutic effect.

Granulocyte-macrophage colony stimulating factor (GM-CSF) is a hematopoietic cell growth factor having pleiotropy and acts to regulate in the developmental and mature stages of granulocytic series and macrophages. GM-CSF also plays a key role in the differentiation of the monocytes in synovial tissues into the inflammatory dendritic cells and involves in inducing and maintaining the emergence and the development of acute arthritis. Meanwhile, the tests of serum and synovium are performed for patients suffering from rheumatoid arthritis. It is found that the level of GM-CSF factor increases significantly and is closely related to disease activity, which is mainly reflected in the deterioration of bone erosion as well as the synovial lining cells and the underlayer cells which are infiltrated with large amount of macrophages.

PD-1 is a key immune checkpoint receptor expressed by the activated T and B cells, and mediates the immunosuppression. PD-1 is a member of the CD28 receptor family, this family includes CD28, CTLA-4, ICOS, PD-1 and BTLA. Two glycoprotein ligands of PD-1 on cell surface, i.e., programmed death ligand-1 (PD-L1) and programmed death ligand-2 (PD-L2), have been identified. They are expressed on the antigen-presenting cells as well as in a variety of human cancers, and they have been shown to downregulate the activation of T cells and the cytokine secretion upon binding to PD-1.

PD-L1 is also referred to as CD274 or B7-H1. PD-L1 has up-regulated expression in a variety of tumor cells, binds to the PD-1 on T cells, inhibits the proliferation and activation of T cells, makes T cells in an inactivated state, and eventually induces the immune escape. The inhibitors of PD-L1 can block the binding of PD-1 and PD-L1, up-regulate the growth and proliferation of T cells, enhance the recognition of T cells to tumor cells, activate its attacking and killing functions, and achieve the anti-tumor effect by mobilizing the immune function of human body itself.

Since monoclonal antibodies such as Adalimumab, the monoclonal antibodies against PD-1, and the monoclonal antibodies against PD-L1 can all be produced by the mammalian expression systems, and the problem that the expression level of the heterologous proteins is low exists in the mammalian expression systems, there is an urgent need to improve the mammalian expression systems known in the prior art and provide a system which is capable of achieving significantly higher expression level of heterologous proteins. Meanwhile, the above-mentioned systems are needed to produce the humanized monoclonal antibodies.

SUMMARY

Technical Problem

The present disclosure provides a DNA sequence which is derived from CHO (Chinese Hamster Ovary) cells and can be used to enhance the expression of the heterologous protein, said DNA sequence is capable of being used for enhancing expression level of the heterologous proteins of the mammalian expression systems.

Solution to Problem

The technical solutions related in the present disclosure are as follows.

(1). A polynucleotide, wherein the polynucleotide is selected from any one of (i) to (iv):

(i) a nucleotide sequence comprising a sequence as shown in any sequence of SEQ ID NOs:3-9;

(ii) a nucleotide sequence comprising a reverse complementary sequence of the sequence as shown in any sequence of SEQ ID NOs:3-9;

(iii) a reverse complementary sequence of a sequence capable of hybridizing with the nucleotide sequence as shown in (i) or (ii) under a high stringency hybridization condition or a very high stringency hybridization condition;

(iv) a sequence having at least 90% sequence identity, alternatively at least 95% sequence identity, preferably at least 97% sequence identity, more preferably at least 98% sequence identity, most preferably at least 99% sequence identity with the nucleotide sequence as shown in (i) or (ii).

(2) The polynucleotide according to (1), wherein the polynucleotide also comprises any one selected from (v) to (viii):

(v) a nucleotide sequence comprising a sequence as shown in SEQ ID NO: 13;

(vi) a nucleotide sequence comprising a reverse complementary sequence of the sequence as shown in SEQ ID NO:13;

(vii) a reverse complementary sequence of a sequence capable of hybridizing with the nucleotide sequence as shown in (v) or (vi) under a high stringency hybridization condition or a very high stringency hybridization condition;

(viii) a sequence having at least 90% sequence identity, alternatively at least 95% sequence identity, preferably at least 97% sequence identity, more preferably at least 98% sequence identity, most preferably at least 99% sequence identity with the nucleotide sequence as shown in (v) or (vi).

(3) The polynucleotide according to (1) or (2), wherein the polynucleotide is capable of increasing the protein expression level of a protein expression system; alternatively, the protein expression system is selected from the protein expression systems of eukaryotic cells; preferably, the protein expression systems of eukaryotic cells are selected from the protein expression systems of CHO (Chinese Hamster Ovary) cells.

(4) The polynucleotide according to (1) or (2), wherein the polynucleotide is selected from a sequence comprising the sequence as shown in SEQ ID NO:4, or a sequence comprising the reverse complementary sequence of the sequence as shown in SEQ ID NO:4; alternatively, the polynucleotide is selected from a nucleotide sequence comprising the sequence as shown in SEQ ID NO:4 and the sequence as shown in SEQ ID NO:13, or a nucleotide sequence comprising the reverse complementary sequence of the sequence as shown in SEQ ID NO:4 and the reverse complementary sequence of the sequence as shown in SEQ ID NO:13.

(5) The polynucleotide according to (3), wherein the protein expression system is used to express an antibody, a fusion protein or a recombinant protein; alternatively, the antibody is selected from monoclonal antibodies, the fusion protein is the antibody against programmed death-1 (PD-1) or the antibody against programmed death-ligand 1 (PD-L1); preferably, the monoclonal antibody is Adalimumab, and said antibody against PD-1 is pembrolizumab.

(6) A WXRE transcriptional regulatory element used for enhancing the protein expression level of a protein expression system, wherein the WXRE transcriptional regulatory element comprises the polynucleotide according to any one of (1) to (5).

(7) A protein expression vector or a protein expression system, wherein the protein expression vector or the protein expression system comprises the polynucleotide according to any one of (1) to (5) or the WXRE transcriptional regulatory element according to (6); alternatively, the protein expression vector or the protein expression system also comprises at least a promoter and at least a restriction enzyme site; preferably, the protein expression vector or the protein expression system is selected from the protein expression vectors of mammalian cells or the protein expression systems of mammalian cells; more preferably, the mammalian cells are CHO cells.

(8) A cell line, wherein the cell line comprises the protein expression vector or the protein expression system according to (7).

(9) A kit, wherein the kit comprises the protein expression vector or the protein expression system according to (7), or the cell line according to (8).

(10) Use of the protein expression vector or the protein expression system according to (7), or the cell line according to (8) in the preparation of a reagent or a kit for detecting an animal disease due to the abnormality of protein expression.

(11) The use according to (10), wherein the animal disease is capable of causing the abnormal expression of a target protein in the animal, and the protein expression vector, or the protein expression system, or the cell line is capable of secreting an antibody of the target protein; alternatively, the animal is selected from mammals; preferably, the mammal is human.

In a technical solution, it can be known from the prior art that, as for rheumatoid arthritis, it is found that the level of GM-CSF factor increases significantly and is closely related to disease activity, mainly reflected in the deterioration of bone erosion as well as the synovial lining cells and the under layer thereof which are infiltrated with large amount of macrophages. Therefore, an antibody of GM-CSF can be prepared and obtained via the protein expression vector or the protein expression system related in the present disclosure, wherein the sequence of the antibody of GM-CSF is known in the prior art. Illustratively, the sequence of the antibody of GM-CSF can be selected from the sequences as shown in WO 2018050111 A1. After the antibody of GM-CSF is obtained, it is used to diagnose rheumatoid arthritis by further detecting the expression level of GM-CSF.

(12) Use of a protein expressed by the protein expression vector or the protein expression system according to (7) or the cell line according to (8) in the preparation of a drug for treating or preventing an animal disease; alternatively, the animal disease is selected from tumors or autoimmune diseases.

(13) The use according to (12), wherein the tumor is selected from cancers, and/or the autoimmune disease is selected from rheumatoid arthritis or ankylosing spondylitis.

(14) A method for preparing a protein, wherein the protein expression vector or the protein expression system according to (7), or the cell line according to (8) is selected to secrete the protein; alternatively, the protein is selected from an antibody, a fusion protein or a recombinant protein; preferably, the antibody is selected from monoclonal antibodies, the fusion protein is the antibody against programmed death-1 (PD-1) or the antibody against programmed death-ligand 1 (PD-L1); more preferably, the monoclonal antibody is Adalimumab, and said antibody against PD-1 is pembrolizumab.

(15) A screening method of a stable cell line highly expressing target protein, wherein a target gene which encodes the target protein is transfected into the cell by using the protein expression vector or the protein expression system according to (7), and the stable cell line highly expressing target protein is screened and obtained; alternatively, the protein expression vector or the protein expression system is selected from the protein expression vectors of mammalian cells or the protein expression systems of mammalian cells; more preferably, the mammalian cells are CHO cells.

(16) The screening method according to (15), wherein the screening method includes antibiotic screenings aiming at selection markers or drug pressure screenings aiming at amplified marker genes.

(17) A cell line, which is obtained by using the screening method according to any one of (15) to (16).

(18) A method for detecting an animal disease, wherein a protein secreted by the protein expression vector or the protein expression system according to (7) or the cell line according to (8) is adopted to detect whether an animal suffers from the disease; wherein the animal disease is capable of causing the abnormal expression of a target protein in the animal; and, (i) if the secreted protein is capable of interacting with the target protein, it indicates that the animal suffers from the disease;

(ii) if the secreted protein is capable of not interacting with the target protein, it indicates that the animal does not suffer from the disease.

(19) The method according to (18), wherein the protein expression vector, or the protein expression system, or the cell line is capable of secreting an antibody of the target protein; alternatively, the animal is selected from mammals; preferably, the mammal is human.

(20) A method of treating or preventing an animal disease, wherein a protein secreted by the protein expression vector or the protein expression system according to (7) or the cell line according to (8) is administered to the animal; alternatively, the animal disease is selected from tumors or autoimmune diseases.

(21) The method according to (20), wherein the tumor is selected from cancers, and/or the autoimmune disease is selected from rheumatoid arthritis or ankylosing spondylitis.

(22) A method of preparing a target antibody, wherein the method includes the following steps:

(i) by the method for preparing a protein according to (14), preparing and obtaining the protein;

(ii) using the protein obtained in step (i) to immunize an animal, so as to obtain the corresponding target antibody.

(23) A vector, wherein the vector comprises at least any one of the polynucleotide according to (1) or (2).

(24) The vector according to (23), wherein the vector also comprises a CMV promoter; alternatively, the CMV promoter comprises a sequence as shown in SEQ ID NO: 16, or the CMV promoter comprises a sequence having at least 90% sequence identity, alternatively at least 95% sequence identity, preferably at least 97% sequence identity, more preferably at least 98% sequence identity, most preferably at least 99% sequence identity with the sequence as shown in SEQ ID NO:16.

(25) The vector according to (23) or (24), wherein the vector comprises one or more genes encoding one or more target proteins.

(26) The vector according to (25), wherein the target protein is selected from a group consisting of an antibody, a fusion protein, an enzyme, a soluble protein, a membrane protein, a structural protein, a ribosome protein, a zymogen, a cell surface receptor protein, a transcriptional regulatory protein, a translational regulatory protein, a chromatin protein, a hormone, a cell cycle regulatory protein, a G protein, a neuroactive peptide, an immunomodulatory protein, a blood component protein, an ion gate protein, a heat shock protein, dihydrofolate reductase, an antibiotic resistance protein, a functional fragment of any one of the target proteins, an epitope fragment of any one of the target proteins, and any combination thereof.

(27) An isolated host cell, wherein the host cell comprises the vector according to any one of (23) to (26).

(28) A method of preparing a host cell which expresses a target protein stably, wherein the method comprises a step of transforming an initial host cell by using the vector according to any one of (23) to (26).

(29) The host cell according to (27) or the method according to (28), wherein the host cell is a Chinese hamster ovary cell.

(30) A method of preparing a target protein, wherein the method comprises preparing the target protein by using the host cell according to (27) or via the method according to (28) or (29).

Alternatively, the present invention provides the following embodiments.

(31). A polynucleotide comprising a nucleotide sequence that is at least 85% identical to a regulatory sequence selected from the group consisting of SEQ ID NOs:3-9, a promotor, and a heterologous sequence that encodes a polypeptide, wherein the regulatory sequence, the promotor, and the heterologous sequence that encodes the polypeptide are operably linked together.

(32). The polynucleotide of (31), wherein the polynucleotide further comprises an EF1αI gene intron.

(33). The polynucleotide of (32), wherein the EF1αI gene intron comprises a sequence that is at least 80% identical to SEQ ID NO: 13.

(34). The polynucleotide of (33), wherein the regulatory sequence selected from the group consisting of SEQ ID NOs: 3-9 has a forward direction.

(35). The polynucleotide of (34), wherein the regulatory sequence selected from the group consisting of SEQ ID NOs: 3-9 has a reverse direction.

(36). A host cell for enhanced expression of an antibody, the cell comprising a first polynucleotide encoding an antibody heavy chain or fragment thereof, wherein the first polynucleotide is operably linked to a sequence that is at least 85% identical to a sequence of any of SEQ ID NOs:3-9 or a reverse complementary sequence of the sequence of any of SEQ ID NOs:3-9; and a second polynucleotide encoding an antibody light chain or fragment thereof, wherein the second polynucleotide is operably linked to a sequence that is at least 85% identical to a sequence of any of SEQ ID NOs:3-9 or a reverse complementary sequence of the sequence of any of SEQ ID NOs:3-9.

(37). The host cell of (36), wherein the first polynucleotide is operably linked to a sequence that is at least 85% identical to SEQ ID NO: 4 and the second polynucleotide is operably linked to a sequence that is at least 85% identical to SEQ ID NO: 4.

(38). The host cell of (36), wherein the first polynucleotide is operably linked to a sequence that is at least 85% identical to SEQ ID NO: 4 and the second polynucleotide is operably linked to a sequence that is at least 85% identical to SEQ ID NO: 9.

(39). The host cell of (36), wherein the first polynucleotide is operably linked to a sequence that is at least 85% identical to SEQ ID NO: 9 and the second polynucleotide is operably linked to a sequence that is at least 85% identical to SEQ ID NO: 9.

(40). The host cell of (36), wherein the first polynucleotide is operably linked to a sequence that is at least 85% identical to SEQ ID NO: 4 and the second polynucleotide is operably linked to a sequence that is at least 85% identical to SEQ ID NO: 17.

(41). The host cell of (36), wherein the first polynucleotide is operably linked to a sequence that is at least 85% identical to SEQ ID NO: 9 and the second polynucleotide is operably linked to a sequence that is at least 85% identical to SEQ ID NO: 17.

(42). An expression vector comprising an expression cassette, wherein the expression cassette comprises a promoter operably linked to a nucleic acid sequence encoding a polypeptide, and a regulatory sequence that is at least 85% identical to a sequence selected from the group consisting of SEQ ID NOs:3-9, wherein the regulatory sequence is operably linked to the promotor.

(43). The expression vector of (42), wherein the expression vector has a sense strand and an anti-sense strand, and the sense strand comprises a sequence (from 5' to 3') that is at least 85% identical to a sequence selected from the group consisting of SEQ ID NOs:3-9.

(44). The expression vector of (42), wherein the expression vector has a sense strand and an anti-sense strand, and the anti-sense strand comprises a sequence (from 5' to 3') that is at least 85% identical to a sequence selected from the group consisting of SEQ ID NOs:3-9.

Effects of Invention

In a technical solution, the use of the transcriptional regulatory element WXRE listed in the present disclosure can greatly increase the expression amount of a heterologous protein and has great contribution to the production of mammalian proteins.

In some technical solutions, the expression amount of a heterologous protein is increased by about or at least 10%, 20%, 30%, 40%, 50%, 60%, 70%, or 80%. In some technical solutions, the expression amount of a heterologous protein is increased up to 80%.

In another technical solution, the use of the transcriptional regulatory element WXRE listed in the present disclosure can enable a heterologous protein to still maintain its biological activity while the expression level is greatly increased.

In another technical solution, the transcriptional regulatory element WXRE listed in the present disclosure is able to be used together with other transcriptional regulatory elements as a whole, and maintains its biochemical activity while enabling the expression level of the heterologous protein to increase greatly.

STATEMENT REGARDING SEQUENCE LISTING

Figure 1:
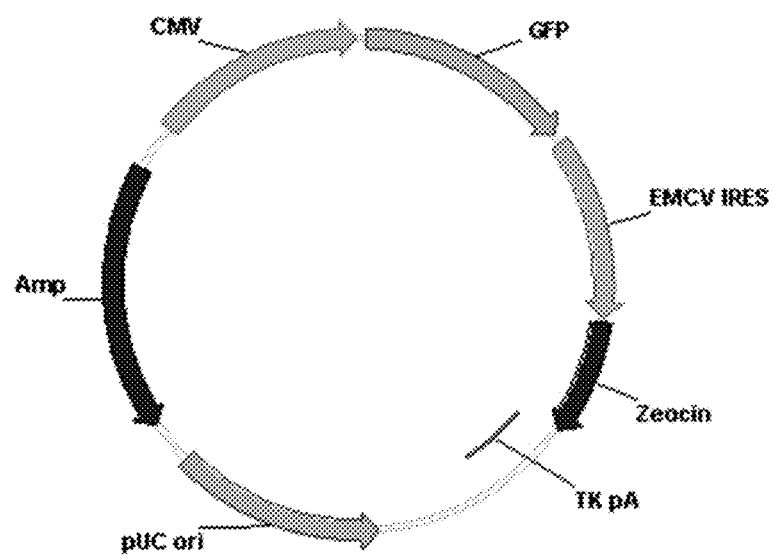
FIG. 1 illustrates a schematic diagram of a GFP-expressing vector without WXRE inserted therein.

The Sequence Listing associated with this application is provided in text form in lieu of a paper copy, and is hereby incorporated by reference into the specification. The name of the text file containing the Sequence Listing is 48771_0003US1_ST25.txt. The text file is 62,989 bytes, and was created and submitted electronically via EFS-Web on Feb. 11, 2021.

DETAILED DESCRIPTION

Definition

When used in the claims and/or the specification, the word "a" or "an" or "the" may refer to "one", but may also refer to "one or more", "at least one" and "one or more than one".

As used in the claims and the specification, the words "comprising", "having", "including" or "containing" means inclusive or open-ended, and does not exclude additional, unrecited elements or method steps. Meanwhile, "comprising", "having", "including" or "containing" may also mean closed-ended, and excludes additional, unrecited elements or method steps.

Throughout this application, the term "about" denotes that a value includes the standard deviation of the error of the device or method used to determine this value.

Although the content disclosed supports that the definition of the term "or" is a substitute only as well as "and/or". Unless it is clearly denoted that it is only a substitute or the substitutes are mutually exclusive, the term "or" in the claims refers to "and/or".

The "transcriptional regulatory element" in the present disclosure refers to some polynucleotides involved in the regulation of gene transcription. Alternatively, the above-mentioned polynucleotide may be selected from DNA(s), which mainly include a promoter, an enhancer, an insulator, and the like. In the present disclosure, the transcriptional regulatory element is also referred to as WXRE (WuXi Regulatory Element). Illustratively, The WXREs in the present disclosure include transcriptional regulatory element A, transcriptional regulatory element B, transcriptional regulatory element C, transcriptional regulatory element D, transcriptional regulatory element E, transcriptional regulatory element F, and transcriptional regulatory element G.

The meaning of the "reverse complementary sequence" in the present disclosure is a sequence which is opposite to the direction of the sequence of the original polynucleotide and is also complementary to the sequence of the original polynucleotide. Illustratively, if the original polynucleotide sequence is ACTGAAC, then the reverse complementary sequence thereof is GTTCAGT.

The "internal ribosomal entry site" (IRES) in the present disclosure belongs to the translational control sequences and is usually located on the 5' end of the gene of interest, and enables the translation of RNA in a cap-independent manner. The transcribed IRES may directly bind to a ribosomal subunit, such that the initiation codon of an mRNA is appropriately oriented in a ribosome to perform translation. The IRES sequence is usually located in the 5'UTR of an mRNA (directly upstream of the initiation codon). IRES functionally replaces the need for various protein factors that interact with the translation mechanism of eukaryotes.

The "vector" in the present disclosure refers to a delivery vehicle for a polynucleotide. In some embodiments, the vector includes a polynucleotide sequence encoding a certain protein operatively inserted therein and enables the expression of this protein in a genetic engineering recombinant technique. The vector can be used to transform, transduce or transfect a host cell, and enable the genetic material element carried by the vector to be expressed in the host cell. The "vector" in the present disclosure may be any suitable vector, which includes chromosomal, non-chromosomal and synthetic nucleic acid vectors (including a group of suitable nucleic acid sequences which express the control elements). Illustratively, said vector may be a recombinant plasmid vector, a recombinant eukaryotic viral vector, a recombinant phage vector, a recombinant yeast minichromosome vector, a recombinant bacterial artificial chromosome vector, or a recombinant yeast plasmid vector.

Illustratively, the vector in the present disclosure may include the derivatives of SV40, bacterial plasmids, phage DNAs, baculovirus, yeast plasmid, vectors derived from a combination of a plasmid and a phage DNA, and vectors such as virus nuclear acids (RNA or DNA). In some embodiments, the vector is an adeno-associated virus (AAV) vector.

In a specific embodiment, the vectors related in the present disclosure are as shown in FIGS. 1 to 2, FIGS. 5 to 6 and FIGS. 8 to 9. In the schematic diagrams of the above-mentioned vectors, the meaning of CMV is human cytomegalovirus promoter (see e.g., PubMed PMID: 2985280), the meaning of TK pA is thymidine kinase polyadenylation signal (see e.g., PubMed PMID: 3018551), the meaning of SV40 is SV40 early promoter (see e.g., PubMed PMID: 6286831), the meaning of BSR is Blasticidin resistance gene: selection marker (see e.g., PubMed PMID: 7948022), the meaning of SV pA is SV40 polyadenylation signal (see e.g., PubMed PMID: 6113054), the meaning of pUC ori is the origin of the replication of pUC plasmid (see e.g., PubMed PMID: 2985470), the meaning of Amp is Ampicillin resistance gene (see e.g., PubMed PMID: 2985470), the meaning of EMCV IRES is the internal ribosomal entry site of encephalomyocarditis virus (see e.g., PubMed PMID: 8954121), the meaning of Zeocin is Zeocin resistance gene: selection marker (see e.g., PubMed PMID: 2450783), and the meaning of EF1αI is the first intron of the gene of human elongation factor 1 alpha (see e.g., PubMed PMID:2210382).

In some embodiments, the CMV promoter in the present disclosure can have a sequence that is at least or about 80%, 85%, 86%, 87%, 88%, 89%, 90%, 91%, 92%, 93%, 94%, 95%, 96%, 97%, 98%, 99% identical to SEQ ID NO:16. As used herein, a promoter refers to a region of DNA that leads to initiation of transcription of a polynucleotide encoding a polypeptide. Promoters are located near the transcription start sites of the coding sequence, upstream on the DNA (towards the 5' region of the sense strand of the coding sequence). In some embodiments, other promotors can be used. In some embodiments, the promotor is a SV40 promoter, hCMV promoter, mCMV promoter, retinoschisin promoter, a rhodopsin promoter, a rhodopsin kinase promoter, a CRX promoter, or an interphotoreceptor retinoid binding protein (IRBP) promoter. Any promoter that allows tissue-specific expression of an encoded protein can also be used.

The "host cell" in the present disclosure refers to a cell having an heterologous polynucleotide and/or a vector introduced therein. Said host cell is a eukaryotic host cell or a prokaryotic host cell, wherein the eukaryotic host cell may be a mammalian host cell, an insect host cell, a plant host cell, a fungal host cell, a eukaryotic algae host cell, a nematode host cell, a protozoan host cell, and a fish host cell. Illustratively, the host cell in the present disclosure is a eukaryotic host cell, and said eukaryotic host cell is a mammalian host cell, wherein said mammalian host cell is selected from a Chinese hamster ovary cell (CHO cell), a COS cell, a Vero cell, a SP2/0 cell, a NS/O myeloma cell, a human embryonic kidney cell, an immature hamster kidney cell, a HeLa cell, a human B cell, a cv-1/EBNA cell, an L cell, a 3T3 cell, a HEPG2 cell, a PerC6 cell, a 293 cell and an MDCK cell. Illustratively, the mammalian host cell in the present disclosure is a CHO cell.

The "protein expression system" in the present disclosure refers to a system comprising a host and a vector containing a heterologous gene, and the purpose of the expression of the heterologous gene in the host can be achieved by this system. The protein expression system generally comprises the following parts: (1) a host, i.e., an organism expressing proteins, which may be selected from bacteria, yeast, plant cells, animal cells, and the like; (2) a vector. The type of the vector matches with the host. According to the different hosts, the vectors are divided into prokaryotic (bacterial) expression vectors, yeast expression vectors, plant expression vectors, mammalian expression vectors, insect expression vectors, and the like. The vector contains a fragment of a heterologous gene. The heterologous gene can be expressed in the host via the mediation of the vector. In some embodiments, the expressed protein products are secreted. In some embodiments, the vectors are integrated into host cell DNA.

A key step in protein expression is the selection of recombinant host cells which have been successfully transfected with the vector comprising the heterologous gene coding the protein of interest. Most commonly a selection marker is included in the vector. The selection marker can be a gene or DNA sequence that allows separation of recombinant host cells containing the marker and those not containing it. The combination of a selection marker and a selection medium allows growth of recombinant host cells that have been transfected with the vector, while prohibiting the growth of host cells that have not been successfully transfected.

Antibiotic resistance genes are the most commonly used markers for recombinant host cell selection. An antibiotic resistance gene as a selection marker, in combination with a selection medium containing the antibiotic, can be used in order to achieve selection. Exemplary antibiotic selection markers include but are not limited to ampicillin resistance gene, chloramphenicol resistance gene, kanamycin resistance gene, tetracycline resistance gene, polymyxin B resistance gene, erythromycin resistance gene, carbenicillin resistance gene, streptomycin resistance gene, spectinomycin resistance gene, blasticidin resistance gene, neomycin resistance gene, puromycin resistance gene, zeocin resistance gene, and hygromycin B resistance gene. Accordingly, the selection antibiotics include but are not limited to ampicillin, chloramphenicol, kanamycin, tetracycline, polymyxin B, erythromycin, carbenicillin, streptomycin, spectinomycin, blasticidin, neomycin, puromycin, zeocin, and hygromycin B. In some embodiments, the selection marker used in the present invention is blasticidin resistance gene. In some embodiments, the selection marker used in the present invention is zeocin resistance gene.

In some aspects, the disclosure provides methods that are designed for quickly evaluating a heteromultimer (e.g., antibody) expression. For example, for efficient expression of antibodies, the antibody heavy chain and the antibody light chain needs to be expressed in roughly 1:1 ratio. If the concentration for a selection antibiotic is too low, the amount of functional vectors in the cells can be too small. If the concentration for a selection antibiotic is too high, it may create a condition that is not favorable for culturing cells. Furthermore, the ratio of the two vectors needs to be properly adjusted. It has been determined, based on tests on many different conditions, the methods provided herein can express antibodies with a high efficiency, and can be used to reliably evaluate the heteromultimer expression in a reasonably short time. Furthermore, the methods provided herein can express antibodies with a high expression level.

In some embodiments, the methods involve transfecting the cell a pair of two vectors, one carrying a heterologous gene encoding a first polypeptide and the other carrying a heterologous gene encoding a second polypeptide. Two selection markers are used. One selection marker is blasticidin resistance gene, and the other selection marker is zeocin resistance gene. In some embodiment, blasticidin is present in the selection medium in an amount of 1-15 μg/mL and zeocin is present in an amount of 50-1500 μg/mL. Preferably, blasticidin is present in an amount of 2-12 μg/mL and zeocin is present in an amount of 100-1000 μg/mL. More preferably, blasticidin is present in an amount of 3-10 μg/mL and zeocin is present in an amount of 150-800 μg/mL. More preferably, blasticidin is present in an amount of 4-9 μg/mL and zeocin is present in an amount of 200-400 μg/mL. Most preferably, blasticidin is present in an amount of 9 μg/mL and zeocin is present in an amount of 400 μg/mL. Alternatively, blasticidin is present in an amount of 4 μg/mL and zeocin is present in an amount of 200 μg/mL. In some embodiments, the ratio of blasticidin concentration to Zeocin concentration is from 1:50~1:40 (e.g., about 9:400). In some embodiments, the minimum concertation of blasticidin in the medium is 5, 6, 7, 8, or 9 μg/mL. In some embodiments, the highest concertation of blasticidin in the medium is 15 or 20 μg/mL.

In some embodiment, the selection medium further comprises serum, polysaccharide (e.g. glucose, and/or dextrose), sodium pyruvate, glutathione, ethanolamine, amino acid (e.g. glycine, alanine, arginine, asparagine, aspartic acid, cysteine, glutamic acid, histidine, isoleucine, leucine, lysine, glutamine, methionine, phenylalanine, proline, serine, threonine, tryptophan, tyrosine, and/or valine) or a salt thereof, vitamin (e.g. ascorbic acid phosphate, choline chloride, D-calcium pantothenate, folic acid, niacinamide, pyridoxine hydrochloride, riboflavin, thiamine hydrochloride, and/or i-inositol), inorganic salt (e.g. calcium chloride, ferric nitrate, magnesium sulfate, potassium chloride, sodium bicarbonate, sodium chloride, and/or sodium phosphate dibasic), protein (e.g. human transferrin and/or recombinant insulin), and/or trace element (e.g. ammonium metavanadate, cupric sulfate, manganous chloride, and/or sodium selenite).

In some embodiments, after about 18~30 hours (e.g., about 24 hours) of transfection, the cells are cultured in an appropriate cell culture medium containing blasticidin (e.g., 9 μg/mL) and Zeocin (e.g., 400 μg/mL). The cells are then passaged to a new medium containing blasticidin and Zeocin every 2 to 4 days. When the cell viability is recovered to 90% or more, the expression level of the heteromultimer can be evaluated by fed-batch cultures. In some embodiments, the fed-batch cultures can be any medium as described herein. In some embodiments, the fed-batch cultures contain blasticidin and Zeocin.

In some embodiments, the "protein expression system" in the present methods involve a pair of two vectors, one carrying a heterologous gene encoding an antibody heavy chain and the other carrying a heterologous gene encoding an antibody light chain. The selection marker in the two vectors might be different. In one embodiment, the selection marker in the first vector is blasticidin while the selection marker in the second vector is zeocin. The concentration of blasticidin and zeocin can be any concentrations as described herein. In some embodiments, the methods can also involve one vector comprising a heterologous gene encoding an antibody heavy chain and a heterologous gene encoding an antibody light chain.

The WXRE sequence can be inserted in the two vectors. They can be the same or different, and can have the forward or reverse directions. Table 1 lists the exemplary combinations of WXREs in the two vectors.

TABLE 1

| Combinations of WXREs | | |
|---|---|---|
| # | WXRE in a first vector | WXRE in a second vector |
| 1 | SEQ ID NO 3 | SEQ ID NO 3 |
| 2 | SEQ ID NO 3 | SEQ ID NO 4 |
| 3 | SEQ ID NO 3 | SEQ ID NO 5 |
| 4 | SEQ ID NO 3 | SEQ ID NO 6 |
| 5 | SEQ ID NO 3 | SEQ ID NO 7 |
| 6 | SEQ ID NO 3 | SEQ ID NO 8 |
| 7 | SEQ ID NO 3 | SEQ ID NO 9 |
| 8 | SEQ ID NO 3 | SEQ ID NO 17 |
| 9 | SEQ ID NO 3 | SEQ ID NO 18 |
| 10 | SEQ ID NO 3 | SEQ ID NO 19 |
| 11 | SEQ ID NO 3 | SEQ ID NO 20 |
| 12 | SEQ ID NO 3 | SEQ ID NO 21 |
| 13 | SEQ ID NO 3 | SEQ ID NO 22 |
| 14 | SEQ ID NO 3 | SEQ ID NO 23 |
| 15 | SEQ ID NO 4 | SEQ ID NO 4 |
| 16 | SEQ ID NO 4 | SEQ ID NO 5 |
| 17 | SEQ ID NO 4 | SEQ ID NO 6 |
| 18 | SEQ ID NO 4 | SEQ ID NO 7 |
| 19 | SEQ ID NO 4 | SEQ ID NO 8 |
| 20 | SEQ ID NO 4 | SEQ ID NO 9 |
| 21 | SEQ ID NO 4 | SEQ ID NO 17 |
| 22 | SEQ ID NO 4 | SEQ ID NO 18 |
| 23 | SEQ ID NO 4 | SEQ ID NO 19 |
| 24 | SEQ ID NO 4 | SEQ ID NO 20 |
| 25 | SEQ ID NO 4 | SEQ ID NO 21 |
| 26 | SEQ ID NO 4 | SEQ ID NO 22 |
| 27 | SEQ ID NO 4 | SEQ ID NO 23 |
| 28 | SEQ ID NO 5 | SEQ ID NO 5 |
| 29 | SEQ ID NO 5 | SEQ ID NO 6 |
| 30 | SEQ ID NO 5 | SEQ ID NO 7 |
| 31 | SEQ ID NO 5 | SEQ ID NO 8 |
| 32 | SEQ ID NO 5 | SEQ ID NO 9 |
| 33 | SEQ ID NO 5 | SEQ ID NO 17 |
| 34 | SEQ ID NO 5 | SEQ ID NO 18 |
| 35 | SEQ ID NO 5 | SEQ ID NO 19 |
| 36 | SEQ ID NO 5 | SEQ ID NO 20 |
| 37 | SEQ ID NO 5 | SEQ ID NO 21 |
| 38 | SEQ ID NO 5 | SEQ ID NO 22 |
| 39 | SEQ ID NO 5 | SEQ ID NO 23 |
| 40 | SEQ ID NO 6 | SEQ ID NO 6 |
| 41 | SEQ ID NO 6 | SEQ ID NO 7 |
| 42 | SEQ ID NO 6 | SEQ ID NO 8 |
| 43 | SEQ ID NO 6 | SEQ ID NO 9 |
| 44 | SEQ ID NO 6 | SEQ ID NO 17 |
| 45 | SEQ ID NO 6 | SEQ ID NO 18 |
| 46 | SEQ ID NO 6 | SEQ ID NO 19 |
| 47 | SEQ ID NO 6 | SEQ ID NO 20 |
| 48 | SEQ ID NO 6 | SEQ ID NO 21 |
| 49 | SEQ ID NO 6 | SEQ ID NO 22 |
| 50 | SEQ ID NO 6 | SEQ ID NO 23 |
| 51 | SEQ ID NO 7 | SEQ ID NO 7 |
| 52 | SEQ ID NO 7 | SEQ ID NO 8 |
| 53 | SEQ ID NO 7 | SEQ ID NO 9 |
| 54 | SEQ ID NO 7 | SEQ ID NO 17 |
| 55 | SEQ ID NO 7 | SEQ ID NO 18 |
| 56 | SEQ ID NO 7 | SEQ ID NO 19 |
| 57 | SEQ ID NO 7 | SEQ ID NO 20 |
| 58 | SEQ ID NO 7 | SEQ ID NO 21 |
| 59 | SEQ ID NO 7 | SEQ ID NO 22 |
| 60 | SEQ ID NO 7 | SEQ ID NO 23 |
| 61 | SEQ ID NO 8 | SEQ ID NO 8 |
| 62 | SEQ ID NO 8 | SEQ ID NO 9 |
| 63 | SEQ ID NO 8 | SEQ ID NO 17 |
| 64 | SEQ ID NO 8 | SEQ ID NO 18 |
| 65 | SEQ ID NO 8 | SEQ ID NO 19 |
| 66 | SEQ ID NO 8 | SEQ ID NO 20 |
| 67 | SEQ ID NO 8 | SEQ ID NO 21 |
| 68 | SEQ ID NO 8 | SEQ ID NO 22 |
| 69 | SEQ ID NO 8 | SEQ ID NO 23 |
| 70 | SEQ ID NO 9 | SEQ ID NO 9 |
| 71 | SEQ ID NO 9 | SEQ ID NO 17 |
| 72 | SEQ ID NO 9 | SEQ ID NO 18 |
| 73 | SEQ ID NO 9 | SEQ ID NO 19 |
| 74 | SEQ ID NO 9 | SEQ ID NO 20 |
| 75 | SEQ ID NO 9 | SEQ ID NO 21 |
| 76 | SEQ ID NO 9 | SEQ ID NO 22 |
| 77 | SEQ ID NO 9 | SEQ ID NO 23 |
| 78 | SEQ ID NO 17 | SEQ ID NO 17 |
| 79 | SEQ ID NO 17 | SEQ ID NO 18 |
| 80 | SEQ ID NO 17 | SEQ ID NO 19 |
| 81 | SEQ ID NO 17 | SEQ ID NO 20 |
| 82 | SEQ ID NO 17 | SEQ ID NO 21 |
| 83 | SEQ ID NO 17 | SEQ ID NO 22 |
| 84 | SEQ ID NO 17 | SEQ ID NO 23 |
| 85 | SEQ ID NO 18 | SEQ ID NO 18 |
| 86 | SEQ ID NO 18 | SEQ ID NO 19 |
| 87 | SEQ ID NO 18 | SEQ ID NO 20 |
| 88 | SEQ ID NO 18 | SEQ ID NO 21 |
| 89 | SEQ ID NO 18 | SEQ ID NO 22 |
| 90 | SEQ ID NO 18 | SEQ ID NO 23 |
| 91 | SEQ ID NO 19 | SEQ ID NO 19 |
| 92 | SEQ ID NO 19 | SEQ ID NO 20 |
| 93 | SEQ ID NO 19 | SEQ ID NO 21 |
| 94 | SEQ ID NO 19 | SEQ ID NO 22 |
| 95 | SEQ ID NO 19 | SEQ ID NO 23 |
| 96 | SEQ ID NO 20 | SEQ ID NO 20 |
| 97 | SEQ ID NO 20 | SEQ ID NO 21 |
| 98 | SEQ ID NO 20 | SEQ ID NO 22 |
| 99 | SEQ ID NO 20 | SEQ ID NO 23 |
| 100 | SEQ ID NO 21 | SEQ ID NO 21 |
| 101 | SEQ ID NO 21 | SEQ ID NO 22 |
| 102 | SEQ ID NO 21 | SEQ ID NO 23 |
| 103 | SEQ ID NO 22 | SEQ ID NO 22 |
| 104 | SEQ ID NO 22 | SEQ ID NO 23 |
| 105 | SEQ ID NO 23 | SEQ ID NO 23 |

The "sequence identity" and the "percent identity" in the present disclosure refer to the percentage of the same (i.e., identical) nucleotides or amino acids between two or more polynucleotides or polypeptides. The sequence identity between two or more polynucleotides or polypeptides can be determined by the following method. The nucleotide sequences or the amino acid sequences of the polynucleotides or polypeptides are aligned and the number of positions containing the same nucleotide or amino acid residue in the aligned polynucleotides or polypeptides is scored and compared with the number of positions containing different nucleotides or amino acid residues in the aligned polynucleotides or polypeptides. The polynucleotides may differ at one position, for example, by containing different nucleotides (i.e., substitutions or mutations) or by the deletion of nucleotide(s) (i.e., the insertion of nucleotide(s) or the deletion of nucleotide(s) in one or two polynucleotides). The polypeptides may differ at one position, for example, by containing different amino acids (i.e., substitutions or mutations) or by the deletion of amino acid(s) (i.e., the insertion of amino acid(s) or the deletion of amino acid(s) in one or two polypeptides). The sequence identity can be calculated by dividing the number of positions containing the same nucleotide or amino acid residue by the total number of the amino acid residues in the polynucleotide or polypeptide. For example, the percent identity can be calculated by dividing the number of positions containing the same nucleotide or amino acid residue by the total number of the nucleotides or the amino acid residues in the polynucleotide or polypeptide and multiplying the result by 100.

The "abnormal expression of a target protein in the animal" in the present disclosure means that, as compared with the expression level of the target protein in the animal under normal condition, the expression level of the target protein in the animal to be tested shows an increase or a decline; or a protein that should not be expressed under normal condition is expressed, or a protein that should be expressed is not expressed. In a technical solution, said animal refers to a mammal. In another technical solution, said mammal is human.

The term "antibody" in the present disclosure refers to an immunoglobulin, a fragment thereof, or a derivative of them, and includes any polypeptide comprising an antigen-binding site, regardless of whether it is produced in vitro or in vivo. This term includes, but is not limited to, a polyclonal antibody, a monoclonal antibody, a monospecific antibody, a bispecific antibody, a trispecific antibody, a multispecific antibody, a non-specific antibody, a humanized antibody, a fully human antibody, a chimeric antibody, a single-domain antibody, a single-stranded antibody, a synthetic antibody, a recombinant antibody, a heterozygous antibody, a mutated antibody, and a grafted antibody. The term "antibody" also includes antibody fragments such as Fab, Fab', F(ab')$_2$, Fv, scFv, Fd, dAb, and other antibody fragments that retain the antigen-binding function. Typically, such fragments will include an antigen-binding fragment.

The "fusion protein" in the present disclosure refers to a molecule comprising two or more proteins or the fragments thereof which are linked by the covalent bond via their respective main chains of the peptides, and more preferably, the fusion protein is generated by the genetic expression of the polynucleotide molecules encoding these proteins. In a preferred embodiment, the fusion protein comprises an immunoglobulin domain. In a preferred embodiment, the fusion protein is an Fc-fusion protein.

Illustratively, the antibodies that may be used in the present disclosure include, but are not limited to, Adalimumab, Bezlotoxumab, Avelumab, Dupilumab, Durvalumab, Ocrelizumab, Brodalumab, Reslizumab, Olaratumab, Daratumumab, Elotuzumab, Necitumumab, Infliximab, Obiltoxaximab, Atezolizumab, Secukinumab, Mepolizumab, Nivolumab, Alirocumab, Evolocumab, Dinutuximab, Bevacizumab, Pembrolizumab, Ramucirumab, Vedolizumab, Siltuximab, Alemtuzumab, Trastuzumab, Pertuzumab, Obinutuzumab, Brentuximab, Raxibacumab, Belimumab, Ipilimumab, Denosumab, Ofatumumab, Besilesomab, Tocilizumab, Canakinumab, Golimumab, Ustekinumab, Certolizumab, Catumaxomab, Eculizumab, Ranibizumab, Panitumumab, Natalizumab, Omalizumab, Cetuximab, Efalizumab, Ibritumomab, Fanolesomab, Tositumomab, Gemtuzumab, Palivizumab, Necitumumab, Basiliximab, Rituximab, Capromab, Satumomab, and Muromonab.

Illustratively, the fusion proteins that may be used in the present disclosure include, but are not limited to, Etanercept, Alefacept, Abatacept, Rilonacept, Romiplostim, Belatacept, and Aflibercept.

In one embodiment, the present disclosure relates to the stringency of hybridization conditions which is used to define the degree of complementarity of two polynucleotides. Alternatively, the above-mentioned polynucleotide may be selected from DNAs. The "stringency" used in the present disclosure refers to the temperature and the ionic strength condition during the hybridization and the presence or absence of certain organic solvents. The higher the stringency, the higher the degree of complementarity between the target nucleotide sequence and the marked polynucleotide sequence. "Stringent conditions" refers to the temperature and the ionic strength condition under which the nucleotide sequence merely having high-frequency complementary bases will hybridize. The term "hybridizes under high stringency or very high stringency conditions" used herein describes the conditions for hybridization and washing. The guidance for performing the hybridization reaction can be found in "Current Protocols in Molecular Biology", John Wiley and Sons, N.Y. (1989), 6.3.1-6.3.6. The specific hybridization conditions mentioned in the present disclosure are as follows: 1) high stringency hybridization conditions: 6× sodium chloride/sodium citrate (SSC) at about 45° C., followed by one or more mashes in 0.2×SSC, 0.1% SDS at 65° C.; 2) very high stringency hybridization conditions: 0.5M sodium phosphate, 7% SDS at 65° C., followed by one or more washes at 0.2×SSC, 1% SDS at 65° C.

In a technical solution of the present disclosure, said WXRE sequence has a sequence identity of at least or about 80%, 81%, 82%, 83%, 84%, 85%, 86%, 87%, 88%, 89%, 90%, 91%, 92%, 93%, 94%, 95%, 96%, 97%, 98%, 99%, or 100% (including all the ranges and percentages between these values) with the sequence of any of SEQ ID NOs: 3-9. In some embodiments, the WXRE sequence has at least or about 1, 2, 3, 4, 5, 6, 7, 9, or 10 conservative mutation relative to a sequence of any of SEQ ID NOs: 3-9. In some embodiments, the WXRE sequence differs from a sequence selected from SEQ ID NOs: 3-9 by at least or about 1, 2, 3, 4, 5, 6, 7, 8, 9, or 10 nucleotides. The WXRE sequence can have a forward direction or a reverse direction. As used herein, a sequence of interest has a forward direction when the sense strand (from 5' to 3') has a sequence that is identical to the sequence of interest. A sequence of interest has a reverse direction when the sense strand has a sequence that is reverse complementary to the sequence of interest. The sequences that are reverse complementary to SEQ ID NOs: 3-9 are set forth in SEQ ID NO: 17-23 respectively. In some embodiments, the disclosure provides a sequence that is at least or about 80%, 81%, 82%, 83%, 84%, 85%, 86%, 87%, 88%, 89%, 90%, 91%, 92%, 93%, 94%, 95%, 96%, 97%, 98%, 99%, or 100% (including all the ranges and percentages between these values) of a sequence selected from SEQ ID NO: 17-23.

In some embodiments, the WXRE sequence can increase the expression amount of an heterologous protein by about or at least 10%, 20%, 30%, 40%, 50%, 60%, 70%, or 80% (e.g., as compared to a control sequence without WXRE sequence).

In a technical solution of the present disclosure, said transcriptional regulatory element may also be selected from a nucleotide sequence comprising a WXRE sequence and other sequences that may increase the level of protein expression of a eukaryotic cell line. Illustratively, the transcriptional regulatory element in the present disclosure is a nucleotide sequence comprising a WXRE sequence and a sequence having sequence identity with the sequence as shown in SEQ ID:13 (the first intron of human EF1αI).

In a technical solution of the present disclosure, said sequence having sequence identity with the sequence as shown in SEQ ID:13 has a sequence identity of at least 80%, 81%, 82%, 83%, 84%, 85%, 86%, 87%, 88%, 89%, 90%, 91%, 92%, 93%, 94%, 95%, 96%, 97%, 98%, 99%, or 100% (including all the ranges and percentages between these values) with the sequence as shown in SEQ ID:13 (the first intron of human EF1αI). In some embodiments, the sequence can increase the expression amount of an heterologous protein by about or at least 10%, 20%, 30%, 40%, 50%, 60%, 70%, or 80% (e.g., as compared to a control sequence without such sequence).

In some embodiments, the WXRE sequence, the promotor, and the polynucleotide encoding a polypeptide are operably linked together. In some embodiments, the WXRE sequence, the promotor, the polynucleotide encoding a polypeptide, and one or more additional regulatory elements are operably linked together. In some embodiments, the one additional regulatory element is an intron of EF1αI (e.g., the first intron of human EF1αI). The WXRE sequence, the promotor, and the polynucleotide encoding a polypeptide that are operably linked together can have various orders. For example, the WXRE sequence can be located before the promotor (e.g., from 5' to 3' on the sense strand of the coding sequence) or after the polynucleotide encoding a polypeptide (e.g., from 5' to 3' on the sense strand of the coding sequence). In some embodiments, there are at least or about 0, 1, 2, 3, 4, 5, 6, 7, 8, 9, 10, 100, 200, 300, 400, 500, 600, 700, 800, 900, 1K, 2K, 3K, 4K or 5K nucleotides between the WXRE sequence and the promoter or between the WXRE sequence and the polynucleotide encoding a polypeptide. In some embodiments, there are no more than 1, 2, 3, 4, 5, 6, 7, 8, 9, 10, 100, 200, 300, 400, 500, 600, 700, 800, 900, 1K, 2K, 3K, 4K or 5K nucleotides between the WXRE sequence and the promoter or between the WXRE sequence and the polynucleotide encoding a polypeptide. In some embodiments, the one or more additional regulatory elements are located between the promoter and the sequence encoding a polypeptide.

The present disclosure also provides methods of enhancing the expression of a recombinant protein or polypeptide. The methods involve inserting one or more vectors as described herein into cells (e.g., by transformation or transfection); culturing the cells in the medium; and recovering the recombinant protein or polypeptide so expressed.

The molecular biological methods adopted in the present disclosure may all be found in the corresponding methods described in the disclosed publications such as "Current Protocols in Molecular Biology" (published by Wiley), "Molecular Cloning: A Laboratory Manual" (published by Cold Spring Harbor Laboratory).

EXAMPLES

Other objects, features and advantages of the present disclosure will become apparent with the following detailed description. However, it should be understood that the detailed description and the specific examples (though representing the specific embodiments of the present disclosure) are provided for illustrative purposes only since various changes and modifications made within the spirit and scope of the present disclosure will become apparent to those skilled in the art after reading this detailed description.

All reagents used in the examples can be purchased and obtained from commercial sources, unless otherwise emphasized.

Example 1: Construction of a Vector Library and Construction of a Stable Pool which Expresses Green Fluorescent Protein 1.1 Preparation of a Vector Library Containing a Genomic Fragment of Chinese Hamster Ovary Cells 1.1.1 1 μg of the GFP-expressing vector (i.e., the vector as shown in FIG. 1) was subjected to enzyme digestion with BamHI in the enzyme digestion kit (NEB) containing the restriction endonuclease BamHI so as to be linearized and stayed overnight at 37° C. (the composition and the contents of the reagents in the enzyme digestion reaction were as shown in Table 2), wherein BamHI could be replaced with any other endonucleases corresponding to a unique restriction site which existed in the upstream of a promoter corresponding to GFP.

The schematic diagram of the GFP-expressing vector was as shown in FIG. 1.

TABLE 2

The composition and the contents of the reagents in the enzyme digestion reaction

| Reaction components | Volume |
| --- | --- |
| NEB CutSmart Buffer (Cat# B7204S) | 5 μL |
| BamHI | 5 μL |
| GFP-expressing vector | 1 μg |
| Ultrapure water | make up to a total volume of 50 μL |

1.1.2 Approximate five million CHO host cells were harvested, a DNeasy Blood & Tissue Kit (QIAGEN) was used to extract the genomic DNA of the CHO host cells, and said genomic DNA was dissolved in 100㎕ of elution buffer inside the above-mentioned kit.

1.1.3 Five micrograms of the genomic DNA was subjected to enzyme digestion with 100 units of restriction endonuclease BglII (NEB) or DpnII (NEB) (the composition and the contents of the reagents in the enzyme digestion reaction were as shown in Table 3). Other restriction endonucleases might also be used, as long as they matched with the cohesive ends of the endonucleases of the linearized vector in step 1.1.1.

TABLE 3

The composition and the contents of the reagents in the enzyme digestion reaction

| Reaction components | Volume |
| --- | --- |
| NEB CutSmart Buffer (Cat# B7204S) | 5 μL |
| BamHI | 5 μL |
| CHO genomic DNA | 1 μg |
| Ultrapure water | make up to a total volume of 50 μL |

1.1.4 The linearized vector in 1.1.1 was treated with 2 units of calf intestinal alkaline phosphatase (NEB) at 37° C. for approximate 30 minutes. Other types of alkaline phosphatases could also be used.

1.1.5 The linearized GFP-expressing vector in 1.1.4 and the digested CHO genomic DNA in 1.1.3 were subjected to separation by agarose gel electrophoresis, respectively. The gel was cut to recover the fragments of the GFP-expressing vector and the 1-4 kb fragments of the digested genome, DNA was extracted from the agarose gel after electrophoresis using a QIAquick Gel Extraction Kit (QIAGEN).

1.1.6 The fragments of the GFP-expressing vector and the fragments of the genome recovered in 1.1.5 were subjected to ligation using a DNA Ligation Kit (Takara, Cat #6022) for 45 minutes at 16° C. (the composition and the contents of the reagents in the ligation reaction were as shown in Table 4).

TABLE 4

The composition and the contents of the reagents in the ligation reaction

| Reaction components | Volume |
|---|---|
| the recovered CHO genomic DNA | 4 μL |
| the recovered vector | 6 μL |
| Solution I | 20 μg |
| Ultrapure water | 10 μL |

1.1.7 Ten microliter of the ligation product obtained by 1.1.6 was taken, 100 μL of competent cells were added, put in the ice bath for 30 minutes, thermally stimulated at 42° C. for 1 minute, and then put on the ice for 1 minute. 500 μL of fresh LB medium free of antibiotic was added to each tube of cells, and the cells were subjected to a 45-minute-recovery at 37° C. The step of plating was skipped and 500 mL of medium containing 100 mg/L of Ampicillin was added directly. The vector extraction was performed using a Plasmid Maxi Kit (QIAGEN). The extracted DNA was used as the vector library.

1.1.8 The vector library obtained in 1.1.7 was linearized using the restriction endonucleases in which the restriction sites were merely located in the prokaryotic region of the backbone of the vector (for example, PvuI (NEB)), and stayed overnight under the same reaction conditions as in 1.1.1 at 37° C. The DNA was recovered by the phenol-chloroform method and used for transfection the next day.

1.2 Construction of the Stable Pool which Expresses Green Fluorescent Protein 1.2.1 Approximate five million CHO host cells were centrifuged, and the supernatant was discarded. At the same time, 90 μL of SF Cell Line Solution and 20 μL of Supplement I in an Amaxa SF Cell Line 4D-Nucleofector Kit L (Lonza, Cat #VCA-1005) and 0.3 μg to 0.6 μg of the linearized vector library obtained by step 1.1.8 were mixed evenly, and the cells were resuspended with this mixed solution and transferred to an electroporation cuvette. The cells were subjected to transfection using a program corresponding to the respective host cells in a 4D-Nucleofector™ System electroporation instrument. The cells after electroporation were suspended with 5 mL of medium free of antibiotic and placed in a shaker at 37° C. for cultivation.

1.2.2 Twenty-four hours after the transfection, equal volume of selective medium containing antibiotic corresponding to the resistance gene in the vector was added in the cell culture (in this experiment, the antibiotic was 800 μg/mL of Zeocin).

1.2.3 The cells were counted every 2 to 4 days. Cell passage was performed according to the growth situation of the cells, and screening was performed by using the selective medium with antibiotic corresponding to the resistance gene in the vector (in this experiment, the antibiotic was 400 μg/mL of Zeocin). Clone screening was prepared when the cell viability recovered to 90% or more.

Example 2: Screening of a Clone Highly Expressing Green Fluorescent Protein 2.1 Single-Cell Sorting and Expansion 2.1.1 The cells in the recovered stable pool in the step 1.2.3 of Example 1 with a higher GFP expression level (for example, the top 0.5% of the expression level) were sorted by a FACS Arial flow cytometer into a 96-well plate for cultivation.

2.1.2 75% of the medium in the plate was changed every 2 to 4 days until the recovered cells were visible by naked eyes.

2.2 Screening for a Clone Highly Expressing GFP

The cells recovered in 2.1.2 were successively transferred into a new 96-well plate respectively, altogether about 300 clones (all the cells in each well were derived from one cell and were referred to as a clone herein). The expression amount of GFP was determined by a FACS Arial flow cytometer, and the clones whose detected intensities were among the top 10% were transferred to a 24-well plate for expansion.

Example 3: Screening, Identification and Verification of the Transcriptional Regulatory Element 3.1 Identification of a Candidate Sequence of the Transcriptional Regulatory Element 3.1.1 When the cells that were expanded to the 24-well plates in 2.2 substantially covered the bottom of the plate, and the DNeasy Blood & Tissue Kit (QIAGEN) was used to extract the genome of each clone.

3.1.2 A forward primer and a reverse primer were respectively designed in the vector (about 200 bp away from the upstream and the downstream of the restriction site of BamHI), and the genomes extracted in 3.1.1 were successively subjected to PCR amplification, wherein the sequence of the forward primer of the PCR reaction was GCAAAAAAGGGAATAAGGGCGACACGG(SEQ ID NO:1) and the sequence of the reverse primer of the PCR reaction was CATAGCCCATATATGGAGTTCCGCGTTA (SEQ ID NO:2).

The reaction system of the above-mentioned PCR reaction was as shown in Table 5.

TABLE 5

The reaction system of the PCR reaction

| Reaction components | Volume |
|---|---|
| 5X Q5 Reaction Buffer | 5 μL |
| 10 mM dNTPs | 0.5 μL |
| 10 μM forward primer | 1.25 μL |
| 10 μM reverse primer | 1.25 μL |
| genome | 1 μL |
| Q5 DNA Polymerase (Cat# M0491S) | 0.25 μL |
| Ultrapure water | 15.75 μL |

The reaction steps of the above-mentioned PCR reaction were as shown in Table 6.

TABLE 6

The reaction steps of the PCR reaction

| Temperature | Time | Number of Cycles |
|---|---|---|
| 98° C. | 1 min | 1 |
| 98° C. | 30 s | |
| 61° C. | 30 s | 35 |
| 68° C. | 5 min | |
| 68° C. | 10 min | 1 |

3.1.3 PCR products were subjected to separation by agarose gel electrophoresis, the gel was cut to recover the specific band(s) of 1 kb or more, and the QIAquick Gel Extraction Kit (QIAGEN) was used to extract DNA.

3.1.4 The recovered band(s) was sent for sequencing, and the sequence A~G of the candidate transcriptional regulatory elements were identified.

3.1.5 The sequence A~G of the transcriptional regulatory elements obtained by sequencing and identification were as follows, wherein the sequence of the transcriptional regulatory element A was the sequence as shown in SEQ ID NO:3 (the reverse complementary sequence of SEQ ID NO: 3 is SEQ ID NO: 17), the sequence of the transcriptional regulatory element B was the sequence as shown in SEQ ID NO:4 (the reverse complementary sequence of SEQ ID NO: 4 is SEQ ID NO: 18), the sequence of the transcriptional regulatory element C was the sequence as shown in SEQ ID NO:5 (the reverse complementary sequence of SEQ ID NO: 5 is SEQ ID NO: 19), the sequence of the transcriptional regulatory element D was the sequence as shown in SEQ ID NO:6 (the reverse complementary sequence of SEQ ID NO: 6 is SEQ ID NO: 20), the sequence of the transcriptional regulatory element E was the sequence as shown in SEQ ID NO:7 (the reverse complementary sequence of SEQ ID NO: 7 is SEQ ID NO: 21), the sequence of the transcriptional regulatory element F was the sequence as shown in SEQ ID NO:8 (the reverse complementary sequence of SEQ ID NO: 8 is SEQ ID NO: 22), the sequence of the transcriptional regulatory element G was the sequence as shown in SEQ ID NO:9 (the reverse complementary sequence of SEQ ID NO: 9 is SEQ ID NO: 23).

Figure 2:
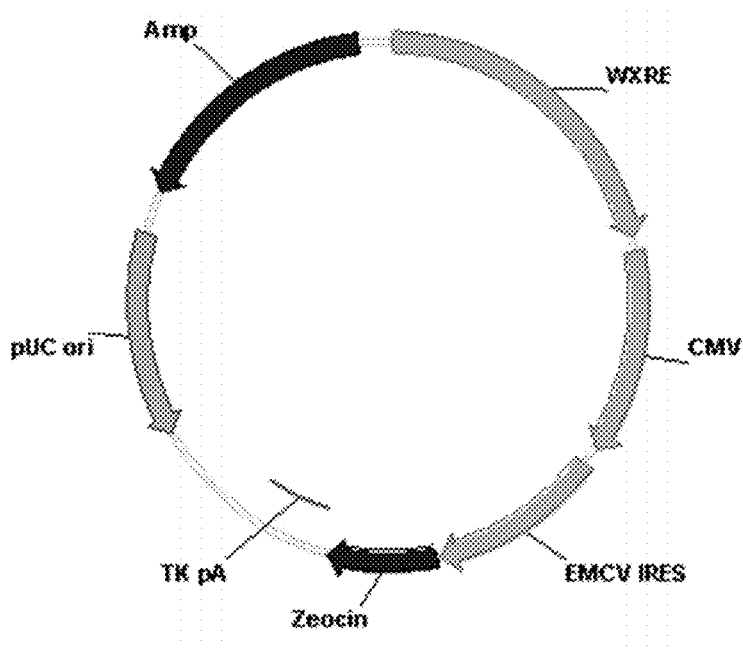
FIG. 2 illustrates a schematic diagram of a GFP-expressing vector with WXRE inserted therein.

3.2 Verification of the Transcriptional Regulatory Element 3.2.1 The transcriptional regulatory element A~G obtained by sequencing and identification in 3.1.5 were respectively inserted into an upstream BamHI restriction site of the corresponding promoter in a vector containing the GFP gene using an In-Fusion Cloning Kit (Takara). A vector with the transcriptional regulatory element inserted therein as shown in FIG. 2 (wherein WXRE showed one of the transcriptional regulatory elements A~G) was obtained. The above-mentioned vector was linearized using the restriction endonucleases in which the restriction sites were merely located in the prokaryotic region of the backbone of the vector (for example, PvuI (NEB)), and stayed overnight at 37° C. DNA was recovered by phenol-chloroform and used for transfection the next day.

3.2.2 Approximate five million CHO host cells were centrifuged, and the supernatant was discarded. At the same time, 90 µL of SF Cell Line Solution and 20 µL of Supplement I in the Amaxa SF Cell Line 4D-Nucleofector Kit L (Lonza, Cat #VCA-1005) and 30 µg of a linearized vector containing the protein to be expressed (obtained by 3.2.1) were mixed evenly, and the cells were resuspended with this mixed solution and transferred to the electroporation cuvette. The cells were subjected to transfection using the program corresponding to the respective host cells in the 4D-Nucleofector™ System electroporation instrument. The cells after electroporation were resuspended with 5 mL of medium free of antibiotic and placed in a shaker at 37° C. for cultivation. Each sample contained one kind of transcriptional regulatory element or was a control without any transcriptional regulatory element.

3.2.3 Twenty-four hours after transfection, equal volume of selective medium containing antibiotic corresponding to the resistance gene in the vector was added in the cell culture. The cells were passaged using a medium containing antibiotic(s) every 2 to 4 days.

3.2.4 After the cell viability recovered to 90% or more, the influence of the transcriptional regulatory element A~G on the expression level of the proteins was evaluated by fed-batch cultures.

Example 4: Influence of the Transcriptional Regulatory Elements on the Expression Level of a Protein Expression System Used to Express an Heterologous Protein 4.1.1 The transcriptional regulatory element A~G were respectively constructed into the upstream BamHI position of the promoter of a fusion protein (the above-mentioned fusion protein was the A chain of PD-L1, whose sequence was the sequence as shown in SEQ ID NO: 10) in both forward and reverse directions. A vector with the transcriptional regulatory element inserted therein as shown in FIG. 2 (wherein WXRE showed one of the transcriptional regulatory element A~G) was obtained, wherein the number after the element name (A~G) indicates the direction of the WXRE regulatory element. The number 1 after the name of the transcriptional regulatory element indicated the forward direction and the number 2 indicated the reverse direction. For example, transcriptional regulatory element A1 showed the forward (i.e., 5' to 3') sequence of the sequence as shown in SEQ ID NO: 3 in the sense strand of coding sequence. Transcriptional regulatory element A2 showed the reverse complementary sequence of the sequence as shown in SEQ ID NO: 17 in the sense strand of protein coding sequence.

The above-mentioned vectors were linearized using the restriction endonucleases in which the restriction sites were merely located in the prokaryotic region of the backbone of the vector (for example, PvuI (NEB)) and stayed overnight under a condition of 37° C. The DNA was recovered by phenol-chloroform and used for transfection the next day.

4.1.2 Approximate five million CHO host cells were centrifuged, and the supernatant was discarded. At the same time, 90 µL of SF Cell Line Solution and 20 µL of Supplement I in the Amaxa SF Cell Line 4D-Nucleofector Kit L (Lonza, Cat #VCA-1005) and 30 µg of the linearized vector containing the fusion protein (obtained by 4.1.1) were mixed evenly, and the cells were resuspended with this mixed solution and transferred to the electroporation cuvette. The cells were subjected to transfection using the program corresponding to the respective host cells in the 4D-Nucleofector™ System electroporation instrument. The cells after electroporation were resuspended with 5 mL of medium free of antibiotic and placed in a shaker at 37° C. for cultivation. Samples in each group only contained one transcriptional regulatory element in a certain direction (i.e., the forward direction or the reverse direction) and a sample which did not contain any transcriptional regulatory element was taken as a control.

4.1.3 Twenty-four hours after transfection, equal volume of medium containing 800 µg/mL of Zeocin was added into the transfected cells.

4.1.4 The cells were passaged using a medium containing 400 µg/mL of Zeocin every 2 to 4 days.

4.1.5 When the cell viability recovered to 90% or more, the expression level of the fusion protein PD-L1 was subjected to evaluation by fed-batch cultures.

4.1.6 Whether the sequence of the PD-L1 obtained by expression was identical to the sequence as shown in SEQ ID NO: 10 was verified.

4.2 Experimental Results

Figure 3:
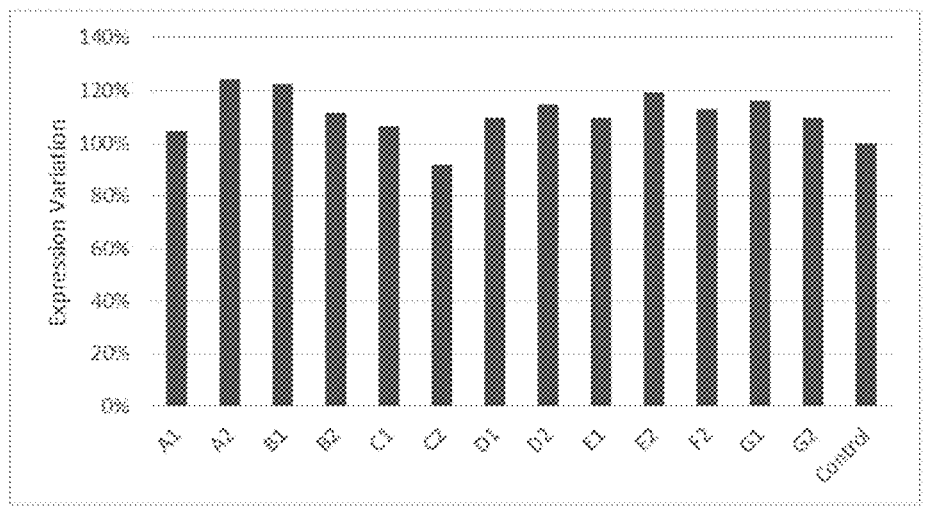
FIG. 3 illustrates the influence on the expression amount of the fusion protein after adding transcriptional regulatory element A~G, wherein A1 and A2 illustrate the forward and reverse directions of transcriptional regulatory element A respectively, and so forth.

As shown in FIG. 3, as compared with the control group which did not have the transcriptional regulatory element, inserting the transcriptional regulatory element in the upstream of the promoter of the fusion protein could increase the expression amount of the target protein by about 10% to 25% (see A2, B1, B2, D2, E2, F2 and G1 in FIG. 3). The promoting effect of the above-mentioned sequence on protein expression in a certain direction was superior to that in the other direction, which might be related to the directionality of the promoter.

Figure 4:
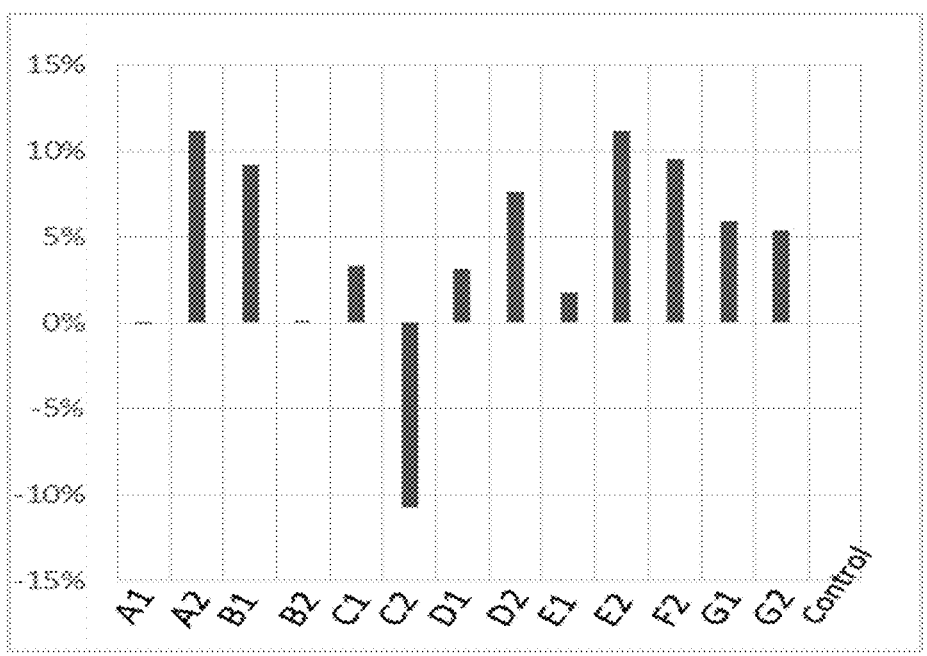
FIG. 4 illustrates the influence on the specific productivity of the expression of the fusion protein after adding transcriptional regulatory element A~G, wherein A1 and A2 illustrate the forward and reverse directions of transcriptional regulatory element A respectively, and so forth.

As shown in FIG. 4, corresponding to the expression amount, the forward direction or the reverse direction of the above-mentioned transcriptional regulatory element could enable an increase about 10% in specific productivity (see A2, B1, B2, D2, E2 and F2 in FIG. 4).

Meanwhile, by verification, the sequence of the PD-L1 obtained by expression was identical to the sequence as shown in SEQ ID NO: 10.

Figure 5:
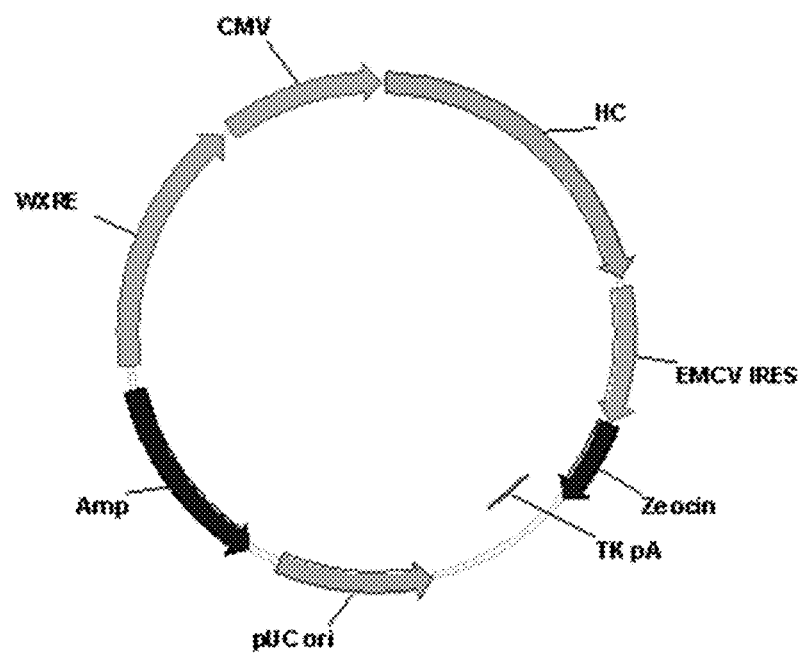
FIG. 5 illustrates a schematic diagram of a vector which expresses the heavy chain of Adalimumab and has WXRE inserted therein, wherein HC means the heavy chain.
Figure 6:
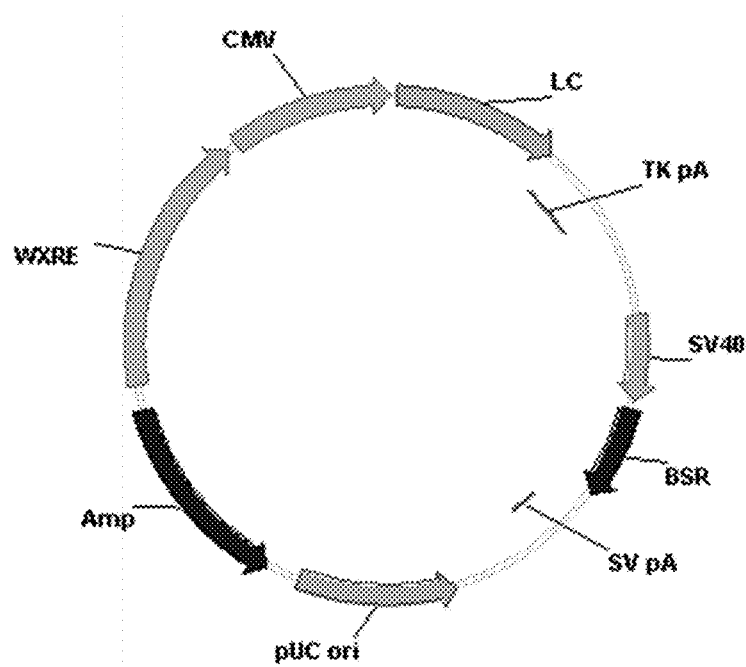
FIG. 6 illustrates a schematic diagram of a vector which expresses the light chain of Adalimumab and has WXRE inserted therein, wherein LC means the light chain.

Example 5: Influence of the Transcriptional Regulatory Elements on the Expression Level of a Protein Expression System Used to Express Adalimumab 5.1.1 The reverse sequence of the transcriptional regulatory element A (A2), the forward sequence of the transcriptional regulatory element B (B1) and the forward sequence of the transcriptional regulatory element G (G1) were respectively constructed into the upstream of the promoter which was located at the upstream of the gene that could express Adalimumab by the In-Fusion Cloning kit of Takara (the specific conditions were as shown in Table 7). Vectors with the transcriptional regulatory element inserted therein as shown in FIG. 5 and FIG. 6 (wherein WXRE showed one of the transcriptional regulatory element A~G) were obtained respectively, wherein the "transcriptional regulatory element in the upstream of the heavy chain" was cloned into the vector as shown in FIG. 5 and the "transcriptional regulatory element in the upstream of the light chain" was cloned into the vector as shown in FIG. 6. Among them, the amino acid sequence of the heavy chain (HC) of Adalimumab in FIG. 5 was as shown in SEQ ID NO:11 and the amino acid sequence of the light chain (LC) of Adalimumab in FIG. 6 was as shown in SEQ ID NO:12.

The above-mentioned vector was linearized using the restriction endonucleases in which the restriction sites were merely located in the prokaryotic region of the backbone of the vector (for example, PvuI (NEB)), and stayed overnight at 37° C. The DNA was recovered by phenol-chloroform and used for transfection the next day.

TABLE 7

Corresponding transcriptional regulatory elements under different conditions

| sample ID | transcriptional regulatory element in the upstream of the heavy chain | transcriptional regulatory element in the upstream of the light chain |
|---|---|---|
| 1 | B1 | B1 |
| 2 | B1 | G1 |
| 3 | G1 | G1 |
| 4 | B1 | A2 |
| 5 | G1 | A2 |
| 6 (control) | N/A | N/A |

5.1.2 Approximate five million CHO host cells were centrifuged, and the supernatant was discarded. At the same time, 90 μL of SF Cell Line Solution and 20 μL of Supplement I in the Amaxa SF Cell Line 4D-Nucleofector Kit L (Lonza, Cat #VCA-1005) and 30 μg of the linearized vector containing the sequence of Adalimumab (obtained by 5.1.1) were mixed evenly, and the cells were resuspended with this mixed solution and transferred to the electroporation cuvette. The cells were subjected to transfection using the program corresponding to the respective host cells in the 4D-Nucleofector™ System electroporation instrument. The cells after electroporation were resuspended with 5 mL of a medium free of antibiotic and placed in a shaker at 37° C. for cultivation. Samples in each group only contained one transcriptional regulatory element in a certain direction (i.e., the forward direction or the reverse direction), and a sample which did not contain any transcriptional regulatory element was taken as a control.

5.1.3 A method that was designed for quickly evaluating antibody expression was used. This method can ensure that the antibody heavy chain and light chain are roughly expressed in 1:1 ratio, and can reliably evaluate the antibody expression in a reasonably short time. Twenty-four hours after transfection, equal volume of medium containing 18 μg/mL of blasticidin and 800 μg/mL of Zeocin was added into the transfected cells.

5.1.4 The cells were passaged using a medium containing 9 μg/mL of blasticidin and 400 μg/mL of Zeocin every 2 to 4 days.

5.1.5 When the cell viability recovered to 90% or more, the expression level of Adalimumab was subjected to evaluation by fed-batch cultures. Since both the heavy chain expression vector and the light chain expression vector of Adalimumab could be transfected into the same host cell, the heavy chain and the light chain of Adalimumab was capable of being expressed simultaneously. Since the heavy chain and the light chain mentioned above were capable of self-assembly in the host cells, a complete Adalimumab was obtained.

5.1.5 The biological activity of the obtained Adalimumab was determined.

5.2 Experimental Results

Figure 7:
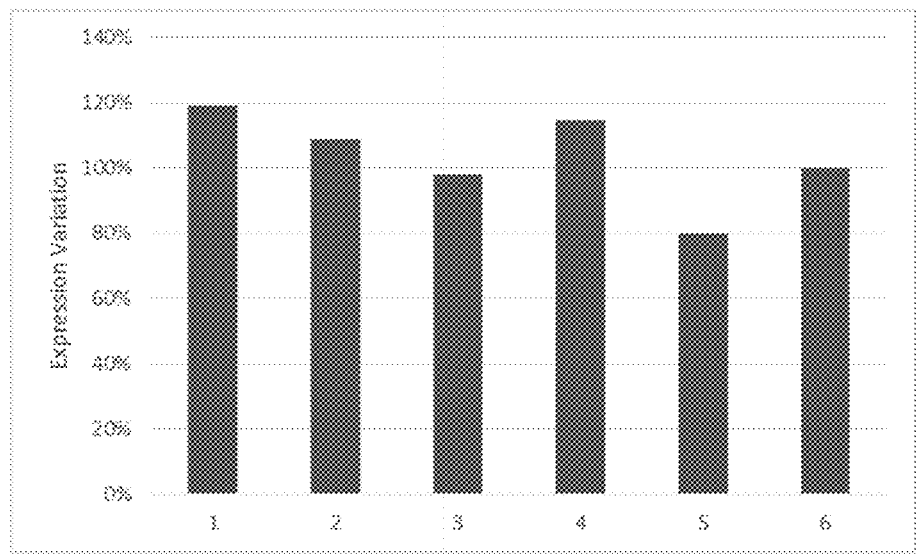
FIG. 7 illustrates a comparison of the expression amount of Adalimumab on $14^{th}$ day under different combined conditions of the transcriptional regulatory elements, wherein in sample 1 to sample 6, the components of the transcriptional regulatory element in the upstream of the heavy chain and the transcriptional regulatory element in the upstream of the light chain are found in Table 6.

As compared with the control group, in part of the forward sequences containing the transcriptional regulatory element B (see sample 1, 2 and 4), the expression level of Adalimumab had an increase of 10% to 20% (as shown in FIG. 7).

By determining the biological activity of Adalimumab expressed by the present heterologous protein expression vector, it was found that its biological activity was identical to the biological activity of the known commercial Adalimumab.

Figure 8:
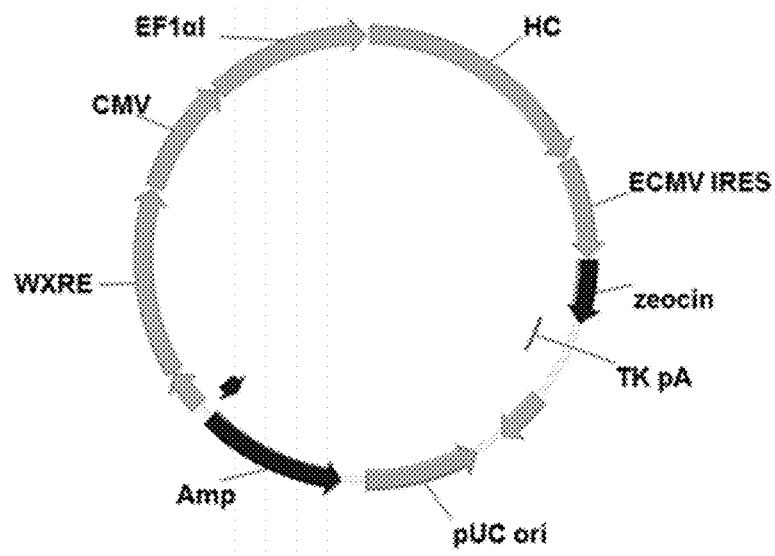
FIG. 8 illustrates a schematic diagram of a vector which expresses the heavy chain of an antibody and comprises WXRE and EF1αI intron (i.e. the sequence as shown in SEQ ID NO: 13) inserted therein, wherein HC means the heavy chain.
Figure 9:
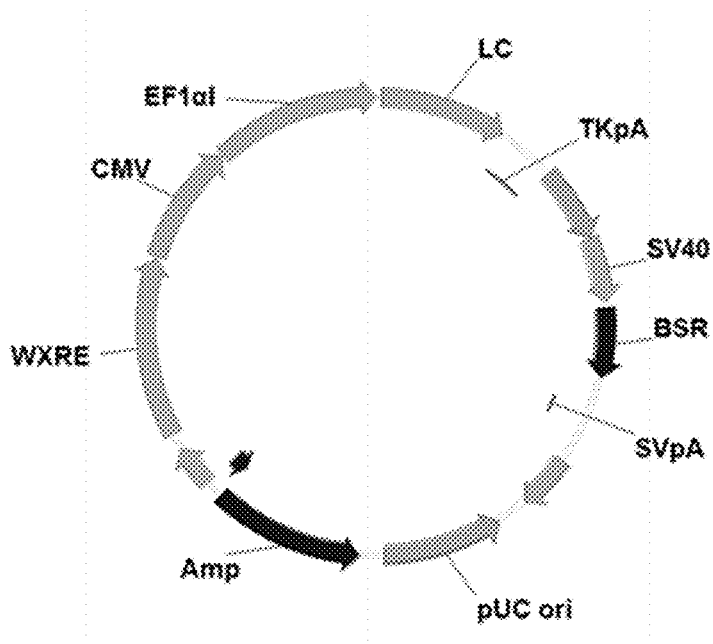
FIG. 9 illustrates a schematic diagram of a vector which expresses the light chain of an antibody and comprises WXRE and EF1αI intron (i.e., the sequence as shown in SEQ ID NO: 13) inserted therein, wherein LC means the light chain.

Example 6: Influence of the Combination of the Transcriptional Regulatory Elements on the Expression Level of a Protein Expression System Used to Express Adalimumab 6.1.1 Two vectors were constructed respectively as illustrated in FIG. 8 and FIG. 9, wherein WXRE is the forward sequence of the transcriptional regulatory element B (B1), EF1αI is the sequence of the first intron of human EF1αI gene as shown in SEQ ID NO: 13, HC is the nucleic acid sequence encoding the heavy chain of Adalimumab, amino acid sequence of which is shown in SEQ ID NO: 11, and LC is the nucleic amino acid sequence encoding the light chain (LC) of Adalimumab, amino acid sequence of which is shown in SEQ ID NO: 12. After completion of the construction of the above-mentioned vectors, plasmid extraction was carried out using an MN kit, and the obtained plasmid was used for cell transfection.

6.1.2 Approximate five million CHO host cells were centrifuged, and the supernatant was discarded. At the same time, 90 μL of SF Cell Line Solution and 20 μL of Supplement I in the Amaxa SF Cell Line 4D-Nucleofector Kit L (Lonza, Cat #VCA-1005) and 30 μg of the vector containing the sequence of Adalimumab (obtained by 6.1.1) were mixed evenly, and the cells were resuspended with this mixed solution and transferred to the electroporation cuvette. The cells were subjected to transfection using the program corresponding to the respective host cells in the 4D-Nucleofector™ System electroporation instrument. The cells after electroporation were resuspended with 5 mL of a medium free of antibiotic and placed in a shaker at 37° C. for cultivation. One group of samples comprised one transcriptional regulatory element, i.e., EF1αI intron, another group of samples comprised two elements, i.e., B1 and EF1αI intron, and a sample free of any transcriptional regulatory element was taken as a control.

6.1.3 24 hours after transfection, equal volume of medium containing 8 μg/mL of blasticidin and 400 μg/mL of Zeocin was added into the transfected cells.

6.1.4 The cells were passaged using a medium containing 4 μg/mL of blasticidin and 200 μg/mL of Zeocin every 2 to 4 days.

6.1.5 When the cell viability recovered to 90% or more, the expression level of Adalimumab was subjected to evaluation by fed-batch cultures. Since both the heavy chain expression vector and the light chain expression vector of Adalimumab could be transfected into the same host cell, the heavy chain and the light chain of Adalimumab was capable of being expressed simultaneously. Since the heavy chain and the light chain mentioned above were capable of self-assembly in the host cells, a complete Adalimumab was obtained.

6.1.6 The biological activity of the obtained Adalimumab was determined.

6.2 Experimental Results

The experimental results of Example 6 were as shown in Table 8.

TABLE 8

Comparison of the relative expression levels of Adalimumab on Day 14 under different combination conditions of the transcriptional regulatory element

| No. | Vector | Relative expression level (Day 14) | Change in expression amount |
|---|---|---|---|
| 1 | CMV (control) | 1 | |
| 2 | CMV-EF1αI | 1.18 | increase by 18% |
| 3 | WXRE-CMV-EF1αI | 1.42 | increase by 42% |

As could be seen from Table 8, the combination comprising WXRE and EF1αI intron significantly increase the expression level of Adalimumab.

By determining the biological activity of Adalimumab expressed by the heterologous protein expression vector, it was found that its biological activity was identical to the biological activity of the known commercial Adalimumab. Thus, the proteins that were expressed by this vector were folded properly.

Example 7: Influence of the Combination of the Transcriptional Regulatory Elements on the Expression Level of a Protein Expression System Used to Express Pembrolizumab 7.1.1 Two vectors were constructed respectively as illustrated in FIG. 8 and FIG. 9, wherein WXRE is the forward sequence of the transcriptional regulatory element B (B1), EF1αI is the sequence of the first intron of human EF1αI gene as shown in SEQ ID NO: 13, HC is the nucleic acid sequence encoding the heavy chain of Pembrolizumab, amino acid sequence of which is shown in SEQ ID NO: 14, and LC is the nucleic amino acid sequence encoding the light chain (LC) of Pembrolizumab, amino acid sequence of which is shown in SEQ ID NO: 15. After completion of the construction of the above-mentioned vectors, plasmid extraction was carried out using an MN kit, and the obtained plasmid was used for cell transfection.

7.1.2 The following experimental steps were same as the experimental steps described in Example 6.1.2 to 6.1.6 of the present disclosure.

7.2 Experimental Results

The experimental results of Example 7 were as shown in Table 9.

TABLE 9

Comparison of the relative expression levels of pembrolizumab on Day 14 under different combination conditions of the transcriptional regulatory element

| No. | Vector | Relative expression level (Day 14) | Change in expression amount |
|---|---|---|---|
| 1 | CMV (control) | 1 | |
| 2 | WXRE-CMV-EF1αI | 1.16 | increase by 16% |

As could be seen from Table 9, the combination comprising WXRE and EF1αI intron significantly increase the expression level of Pembrolizumab.

By determining the biological activity of Pembrolizumab expressed by the heterologous protein expression vector, it was found that its biological activity was identical to the biological activity of the known commercial Pembrolizumab.

Figure 10:
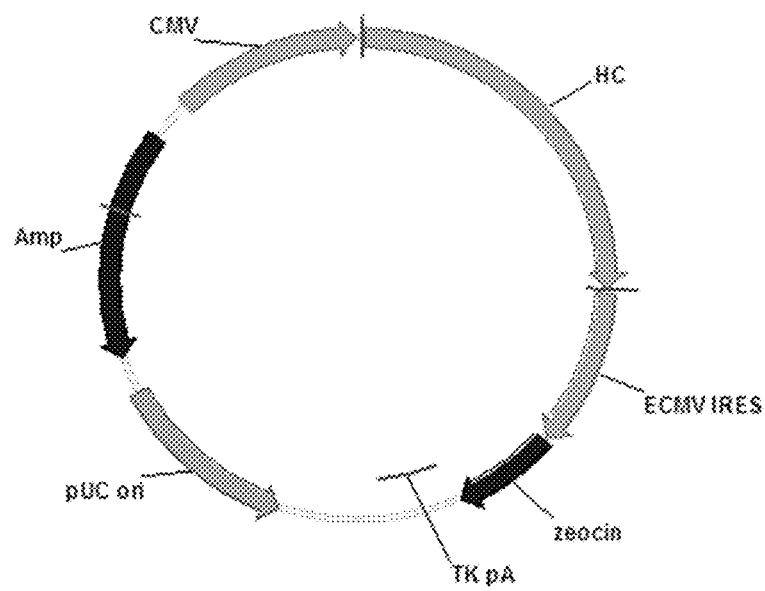
FIG. 10 illustrates a schematic diagram of a vector which expresses an antibody heavy chain.
Figure 11:
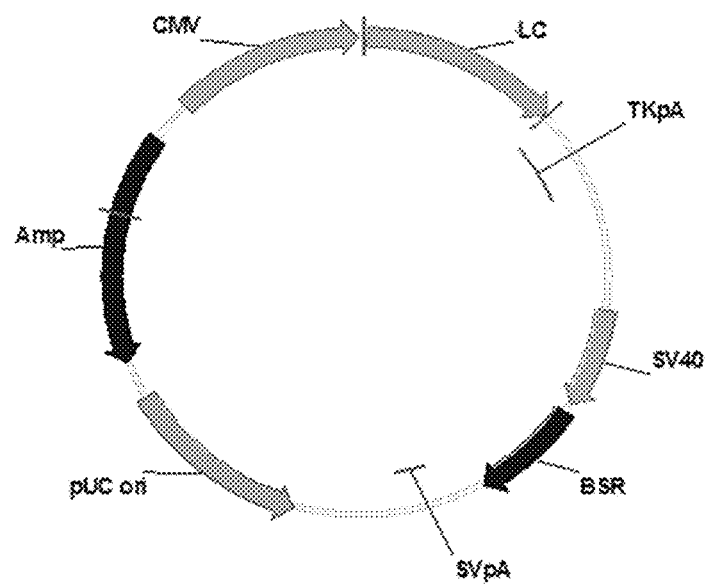
FIG. 11 illustrates a schematic diagram of a vector which expresses an antibody light chain.

Example 8: Influence of Different Antibiotic Concentrations on Expression Level of a Protein Expression System 8.1.1 Two sets of vectors were constructed respectively as illustrated in FIG. 10 and FIG. 11. One set is for Adalimumab and the other is for Pembrolizumab. After completion of vector construction, plasmid extraction was carried out using an MN kit, and the obtained plasmid was used for cell transfection.

8.1.2 Approximate five million CHO host cells were centrifuged, and the supernatant was discarded. At the same time, 90 μL of SF Cell Line Solution and 20 μL of Supplement I in the Amaxa SF Cell Line 4D-Nucleofector Kit L (Lonza, Cat #VCA-1005) and 30 μg of the vector containing the sequence of Adalimumab or Pembrolizumab were mixed evenly, and the cells were resuspended with this mixed solution and transferred to the electroporation cuvette. The cells were subjected to transfection using the program corresponding to the respective host cells in the 4D-Nucleofector™ System electroporation instrument. The cells after electroporation were resuspended with 5 mL of a medium free of antibiotic and placed in a shaker at 37° C. for cultivation.

8.1.3 24 hours after transfection, the cells were passaged using a selection medium containing different concentrations of Blasticidin and/or Zeocin every 2 to 4 days. The specific concentrations of Blasticidin and/or Zeocin are listed in Table 10.

8.1.4 When the cell viability recovered to 90% or more, the antibody expression level of was subjected to evaluation by fed-batch cultures. Since both the heavy chain expression vector and the light chain expression vector could be transfected into the same host cell, the antibody heavy chain and light chain were capable of being expressed simultaneously. Since the heavy chain and the light chain were capable of self-assembly in the host cells, a complete antibody was obtained.

8.1.5 The biological activity of the obtained antibodies was determined.

8.2 Experimental Results

The experimental results of Example 8 were shown in Table 10.

TABLE 10

Comparison of expression levels of Adalimumab and Pembrolizumab on Day 14 under different antibiotic concentrations

| | | Blasticidin Concentration (µg/mL) | Zeocin Concentration (µg/mL) | Titer (g/L) |
|---|---|---|---|---|
| Adalimumab | 1 | 9 | 0 | 0.66 |
| | 2 | 0 | 400 | 1.14 |
| | 3 | 9 | 400 | 1.35 |
| | 4 | 4 | 200 | 1.24 |
| Pembrolizumab | 1 | 9 | 0 | 0.69 |
| | 2 | 0 | 400 | 1.99 |
| | 3 | 9 | 400 | 2.27 |
| | 4 | 4 | 200 | 2.15 |

As could be seen from Table 10, the combination comprising Blasticidin and Zeocin attained a significantly increased expression level, as compared to the sole use of Blasticidin or Zeocin.

By determining the biological activity of Adalimumab or Pembrolizumab expressed by the heterologous protein expression vector, it was found that its biological activity was identical to the biological activity of the known commercial Adalimumab or Pembrolizumab. Thus, the proteins that were expressed by this vector were folded properly.

The above-mentioned examples of the present disclosure are examples provided for clearly illustrating the present disclosure only and are not limitations to the embodiments of the present disclosure. For those of ordinary skill in the art, other changes or variations in different forms may also be made on the basis of the above-mentioned specification. There is no need and no way to exhaust all of the embodiments herein. Any modifications, equivalent substitutions, improvements, and the like made within the spirit and principle of the present disclosure should all be included within the protection scope of the claims of the present disclosure.

The invention claimed is:

1. A vector comprising a heterologous nucleotide sequence and a nucleotide sequence selected from the group consisting of (i) to (ii):
   (i) a sequence of any of SEQ ID NOs: 3-9; and
   (ii) a reverse complementary sequence of the sequence of any of SEQ ID NOs: 3-9.

2. The vector of claim 1, wherein the vector is a recombinant expression vector.

3. The vector of claim 1, further comprising a nucleotide sequence selected from the group consisting of (iii) to (iv):
   (iii) a sequence having at least 80% sequence identity with SEQ ID NO: 13; and
   (iv) a sequence having at least 80% sequence identity with a reverse complementary sequence of SEQ ID NO: 13.

4. The vector of claim 1, further comprising a CMV promoter.

5. The vector of claim 4, wherein the CMV promoter comprises a nucleotide sequence having at least 80% sequence identity with SEQ ID NO: 16.

6. The vector of claim 4, wherein the CMV promoter comprises a nucleotide sequence having at least 90% sequence identity with SEQ ID NO: 16.

7. The vector of claim 4, wherein the CMV promoter comprises a nucleotide sequence that is identical to SEQ ID NO: 16.

8. The vector of claim 3, wherein the nucleotide sequence selected from the group consisting of (iii) to (iv) has at least 90% sequence identity with SEQ ID NO: 13.

9. The vector of claim 3, wherein the nucleotide sequence selected from the group consisting of (iii) to (iv) is identical to SEQ ID NO: 13.

10. The vector of claim 1, wherein the nucleotide sequence selected from the group consisting of (i) to (ii) is SEQ ID NO: 3.

11. The vector of claim 1, wherein the nucleotide sequence selected from the group consisting of (i) to (ii) is SEQ ID NO: 4.

12. The vector of claim 1, wherein the nucleotide sequence selected from the group consisting of (i) to (ii) is SEQ ID NO: 5.

13. The vector of claim 1, wherein the nucleotide sequence selected from the group consisting of (i) to (ii) is SEQ ID NO: 6.

14. The vector of claim 1, wherein the nucleotide sequence selected from the group consisting of (i) to (ii) is SEQ ID NO: 7.

15. The vector of claim 1, wherein the nucleotide sequence selected from the group consisting of (i) to (ii) is SEQ ID NO: 8.

16. The vector of claim 1, wherein the nucleotide sequence selected from the group consisting of (i) to (ii) is SEQ ID NO: 9.

17. A vector comprising a nucleotide sequence that has at least 90% sequence identity with SEQ ID NO: 13 and a nucleotide sequence selected from the group consisting of (i) to (ii):
   (i) a sequence of any of SEQ ID NOs: 3-9; and
   (ii) a reverse complementary sequence of the sequence of any of SEQ ID NOs: 3-9.

18. The vector of claim 17, wherein the vector further comprises a CMV promoter.

19. A vector comprising a CMV promoter and a nucleotide sequence selected from the group consisting of (i) to (ii):
   (i) a sequence of any of SEQ ID NOs: 3-9; and
   (ii) a reverse complementary sequence of the sequence of any of SEQ ID NOs: 3-9.

20. The vector of claim 19, wherein the CMV promoter comprises a nucleotide sequence having at least 80% sequence identity with SEQ ID NO: 16.

* * * * *